(12) United States Patent
Sel et al.

(10) Patent No.: US 8,247,544 B2
(45) Date of Patent: Aug. 21, 2012

(54) METHOD FOR PRODUCING A CELL AND/OR TISSUE AND/OR DISEASE PHASE SPECIFIC MEDICAMENT

(75) Inventors: Serdar Sel, Marburg (DE); Harald Renz, Marburg-Cappel (DE)

(73) Assignee: Sterna Biologicals GmbH & Co. KG, Marburg (DE)

( * ) Notice: Subject to any disclaimer, the term of this patent is extended or adjusted under 35 U.S.C. 154(b) by 0 days.

(21) Appl. No.: 13/037,411

(22) Filed: Mar. 1, 2011

(65) Prior Publication Data

US 2011/0190377 A1    Aug. 4, 2011

Related U.S. Application Data

(62) Division of application No. 10/574,560, filed as application No. PCT/DE2004/002197 on Oct. 1, 2004.

(30) Foreign Application Priority Data

Oct. 2, 2003   (DE) .................................. 103 46 487

(51) Int. Cl.
*C07H 21/04*  (2006.01)
*A61K 48/00*  (2006.01)

(52) U.S. Cl. ...................... 536/24.5; 536/23.1; 514/44

(58) Field of Classification Search .................. None
See application file for complete search history.

(56) References Cited

U.S. PATENT DOCUMENTS 7,355,035 B1   4/2008  Atkins et al.

FOREIGN PATENT DOCUMENTS

| WO | 00/09672 | 2/2000 |
| WO | 00/51621 | 9/2000 |
| WO | 01/11023 | 2/2001 |
| WO | 02/068637 | 9/2002 |

OTHER PUBLICATIONS

S.W.Santoro; A general purpose RNA-cleaving . . . ; Nat. Acad. Sci.; vol. 94; Apr. 1997; pp. 4262-4266.
L.Q.Sun; Catalytic nucleic acids . . . ; Pharma. Reviews; Williams & Wilkins Inc.; Sep. 2000; pp. 325-347.
S.Imagawa; Negative regulation of the erythropoietin gene . . . ; Blood, W.B. Saunders; Feb. 1997; pp. 1430-1439.

*Primary Examiner* — Amy Bowman
(74) *Attorney, Agent, or Firm* — Jonathan Myers; Andrew Wilford

(57) ABSTRACT

A DNAzyme is disclosed, which comprises:
(i) a catalytic domain with a nucleotide sequence GGCTAGCTACAACGA or a modified sequence of comparable biological effect, which cleaves T-bet mRNA at every purine-pyrimidine binding site to which it is bound;
(ii) a right substrate binding domain which is contiguous with the 3'-end of the catalytic domain; and
(iii) a left substrate binding domain which is contiguous with the 5'-end of the catalytic domain, whereby the two substrate binding domains are respectively complementary to two regions of the T-bet mRNA so that they hybridize with the mRNA;
are active in vivo; and
contain the sequences td 69 GGCAATGAA GGC TAGCTACAACGA TGGGTTTCT or td70 TCACGGCAA GGCTAGCTACAACGA GAACTGGGT.

8 Claims, 10 Drawing Sheets

| Name | DNAzyme Sequence |
|---|---|
| SEQ ID NO. 71 td1 | TGGCTTCTAggctagctacaacgaGCCCTCGTC |
| SEQ ID NO. 72 td2 | GGGCTCTGAggctagctacaacgaGCCTGGCTT |
| SEQ ID NO. 73 td3 | GGGACCCCAggctagctacaacgaCGGAGCCCG |
| SEQ ID NO. 74 td4 | GGTGGGGAggctagctacaacgaCCCACCGGA |
| SEQ ID NO. 75 td5 | GGCGGGGAggctagctacaacgaCCGAGGGCC |
| SEQ ID NO. 76 td6 | GGGCTGGGAggctagctacaacgaGGGCAGGGA |
| SEQ ID NO. 77 td7 | CGTCGAGGAggctagctacaacgaCCGCCCCTC |
| SEQ ID NO. 78 td8 | GGGCTGGCAggctagctacaacgaCTTCCCGTA |
| SEQ ID NO. 79 td9 | CGATGCCCAggctagctacaacgaCCGGGGCGG |
| SEQ ID NO. 80 td10 | GCTCCACGAggctagctacaacgaGCCCATCCG |
| SEQ ID NO. 81 td11 | CCGGCTCCAggctagctacaacgaGATGCCCAT |
| SEQ ID NO. 82 td12 | TCTCCGCAAggctagctacaacgaCCGGCTCCA |
| SEQ ID NO. 83 td13 | CCGTCAGCAggctagctacaacgaGTCTCCGCA |
| SEQ ID NO. 84 td14 | TCCCCGGCAggctagctacaacgaCGGCTCGGT |
| SEQ ID NO. 85 td15 | CCCCCGCGAggctagctacaacgaGCTCGTCCG |
| SEQ ID NO. 86 td16 | GTAGGGAGAggctagctacaacgaCCCAGGCTG |
| SEQ ID NO. 87 td17 | GGGCGGGCAggctagctacaacgaCAAGGCGCC |
| SEQ ID NO. 88 td18 | CGGGAAGGAggctagctacaacgaTCGCCCGCG |
| SEQ ID NO. 89 td19 | TAGTCCTCAggctagctacaacgaGCGGCCCCG |
| SEQ ID NO. 90 td20 | TCCCCGACAggctagctacaacgaCTCCAGTCC |
| SEQ ID NO. 91 td21 | TTTCCCCGAggctagctacaacgaACCTCCAGT |
| SEQ ID NO. 92 td22 | TGAGCGCGAggctagctacaacgaCCTCAGTTT |
| SEQ ID NO. 93 td23 | GGACCACAAggctagctacaacgaAGGTGGTTG |
| SEQ ID NO. 94 td24 | CTTGGACCAggctagctacaacgaAACAGGTGG |
| SEQ ID NO. 95 td25 | AAACTTGGAggctagctacaacgaCACAACAGG |
| SEQ ID NO. 96 td26 | CTGATTAAAggctagctacaacgaTTGGACCAC |
| SEQ ID NO. 97 td27 | TGGTGCTGAggctagctacaacgaTAAACTTGG |
| SEQ ID NO. 98 td28 | TGATGATCAggctagctacaacgaCTCTGTCTG |
| SEQ ID NO. 99 td29 | TGGTGATGAggctagctacaacgaCATCTCTGT |
| SEQ ID NO. 100 td30 | GCTTGGTGAggctagctacaacgaGATCATCTC |
| SEQ ID NO. 101 td31 | ATGGGAACAggctagctacaacgaCCGCCGTCC |
| SEQ ID NO. 102 td32 | GAATGGGAAggctagctacaacgaATCCGCCGT |
| SEQ ID NO. 103 td33 | TGACAGGAAggctagctacaacgaGGGAACATC |
| SEQ ID NO. 104 td34 | AGTAAATGAggctagctacaacgaAGGAATGGG |
| SEQ ID NO. 105 td35 | CACAGTAAAggctagctacaacgaGACAGGAAT |
| SEQ ID NO. 106 td36 | GCCCGGCCAggctagctacaacgaAGTAAATGA |
| SEQ ID NO. 107 td37 | CCACAAACAggctagctacaacgaCCTGTAGTG |
| SEQ ID NO. 108 td38 | GTCCACAAAggctagctacaacgaATCCTGTAG |
| SEQ ID NO. 109 td39 | CCACGTCCAggctagctacaacgaAAACATCCT |
| SEQ ID NO. 110 td40 | CCAAGACCAggctagctacaacgaGTCCACAAA |
| SEQ ID NO. 111 td41 | CCACCAAGAggctagctacaacgaCACGTCCAC |
| SEQ ID NO. 112 td42 | GCTGGTCCAggctagctacaacgaCAAGACCAC |
| SEQ ID NO. 113 td43 | GCTCTGGTAggctagctacaacgaCGCCAGTGG |
| SEQ ID NO. 114 td44 | CTGCACCCAggctagctacaacgaTTGCCGCTC |
| SEQ ID NO. 115 td45 | CACACTGCAggctagctacaacgaCCACTTGCC |
| SEQ ID NO. 116 td46 | CTTTCCACAggctagctacaacgaTGCACCCAC |
| SEQ ID NO. 117 td47 | GCCTTTCCAggctagctacaacgaACTGCACCC |
| SEQ ID NO. 118 td48 | TTCCTGGCAggctagctacaacgaGCTGCCCTC |

*FIG. 3*

| Name | DNAzyme Sequence |
|---|---|

| | | |
|---|---|---|
| SEQ ID NO. 149 | TD49 | GTGGACGTAggctagctacaacgaAGGCGGTTT |
| SEQ ID NO. 150 | TD50 | CCGCGTGGAggctagctacaacgaGTACAGGCG |
| SEQ ID NO. 151 | TD51 | CCTGGCGCAggctagctacaacgaCCAGTGCGC |
| SEQ ID NO. 152 | TD52 | CAAATGAAAggctagctacaacgaTTCCTGGCG |
| SEQ ID NO. 153 | TD53 | TTTCCCAAAggctagctacaacgaGAAACTTCC |
| SEQ ID NO. 154 | TD54 | ATTGTTGGAggctagctacaacgaGCCCCCTTG |
| SEQ ID NO. 155 | TD55 | TGGGTCACAggctagctacaacgaTGTTGGACG |
| SEQ ID NO. 156 | TD56 | TCTGGGTCAggctagctacaacgaATTGTTGGA |
| SEQ ID NO. 157 | TD57 | GCACAATCAggctagctacaacgaCTGGGTCAC |
| SEQ ID NO. 158 | TD58 | GGAGCACAAggctagctacaacgaCATCTGGGT |
| SEQ ID NO. 159 | TD59 | ACTGGAGCAggctagctacaacgaAATCATCTG |
| SEQ ID NO. 160 | TD60 | ATGGAGGGAggctagctacaacgaTGGAGCACA |
| SEQ ID NO. 161 | TD61 | TGGTACTTAggctagctacaacgaGGAGGGACT |
| SEQ ID NO. 162 | TD62 | GGGCTGGTAggctagctacaacgaTTATGGAGG |
| SEQ ID NO. 163 | TD63 | TCAACGATAggctagctacaacgaGCAGCCGGG |
| SEQ ID NO. 164 | TD64 | CCTCAACGAggctagctacaacgaATGCAGCCG |
| SEQ ID NO. 165 | TD65 | TCACCTCAAggctagctacaacgaGATATGCAG |
| SEQ ID NO. 166 | TD66 | CGTCGTTCAggctagctacaacgaCTCAACGAT |
| SEQ ID NO. 167 | TD67 | GTAAAGATAggctagctacaacgaGCCGTGTTCG |
| SEQ ID NO. 168 | TD68 | AAGTAAAGAggctagctacaacgaATGCGTGTT |
| SEQ ID NO. 169 | TD69 | GGCAATGAAggctagctacaacgaTGCGTTTCT |
| SEQ ID NO. 170 | TD70 | TCACGGCAAggctagctacaacgaGAACTGGTT |
| SEQ ID NO. 171 | TD71 | AGGCAGTCAggctagctacaacgaGGCAATGAA |
| SEQ ID NO. 172 | TD72 | ATCTCGGCAggctagctacaacgaTCTGGTAGG |
| SEQ ID NO. 173 | TD73 | GCTGAGTAAggctagctacaacgaCTCGGCATT |
| SEQ ID NO. 174 | TD74 | TATTATCAAggctagctacaacgaTTCAGCTG |
| SEQ ID NO. 175 | TD75 | GGGTTATTAggctagctacaacgaCAATTTCA |
| SEQ ID NO. 176 | TD76 | AAGGGGTTAggctagctacaacgaTATCAATTT |
| SEQ ID NO. 177 | TD77 | CTCCCGGAAggctagctacaacgaCCTTTGGCA |
| SEQ ID NO. 178 | TD78 | GTACATGGAggctagctacaacgaTCAAAGTTC |

FIG. 3 Cont.

Multiple Sequence Alignments T-bet

| | | | | |
|---|---|---|---|---|
| SEQ ID NO. 149 | | 1 | CGGCCCGCTGGAGAGGAAGCCCGAGAGCTGCCGCGCGCCTGCCGGACGAGGGCGTAGAAG | 60 |
| SEQ ID NO. 150 | Seq_2 | 1 | CGGCCCGCTGGAGAGGAAGCCCGAGAGCTGCCGCGCGCCTGCCGGACGAGGGCGTAGAAG | 60 |
| SEQ ID NO. 149 | | 61 | CCAGGCGTCAGAGCCCGGGCTCCGGTGGGGTCCCCACCCGGCCCTCGGGTCCCCCGCCC | 120 |
| SEQ ID NO. 150 | Seq_2 | 61 | CCAGGCGTCAGAGCCCGGGCTCCGGTGGGGTCCCCACCCGGCCCTCGGGTCCCCCGCCC | 120 |
| SEQ ID NO. 149 | | 121 | CCTGCTCCCTGCC␣ATCCCAGCCCACGCGACCCTCTCGCGCGCGAGGGGCGGGTCCTCG | 180 |
| SEQ ID NO. 150 | Seq_2 | 121 | CCTGCTCCCTGCC␣ATCCCAGCCCACGCGACCCTCTCGCGCGCGAGGGGCGGGTCCTCG | 180 |
| SEQ ID NO. 149 | | 181 | ACGGCTACGGGAAGGTGCCAGCCCGCCCCGGATGGGCATCGTGGAGCCGGGTTGCGGAGA | 240 |
| SEQ ID NO. 150 | Seq_2 | 181 | ACGGCTACGGGAAGGTGCCAGCCCGCCCCGGATGGGCATCGTGGAGCCGGGTTGCGGAGA | 240 |
| SEQ ID NO. 149 | | 241 | CATGCTGACGGGCACCGAGCCGATGCCGGGGAGCGACGAGGGCCGGGCGCCTGGCGCCGA | 300 |
| SEQ ID NO. 150 | Seq_2 | 241 | CATGCTGACGGGCACCGAGCCGATGCCGGGGAGCGACGAGGGCCGGGCGCCTGGCGCCGA | 300 |
| SEQ ID NO. 149 | | 301 | CCCGCAGCA␣CGCTACTTCTACCCGGAGCCGGGCGCGCAGGACGCGGACGAGCGTCGCGG | 360 |
| SEQ ID NO. 150 | Seq_2 | 301 | CCCGCAGCA␣CGCTACTTCTACCCGGAGCCGGGCGCGCAGGACGCGGACGAGCGTCGCGG | 360 |
| SEQ ID NO. 149 | | 361 | GGGCGGCAGCCTGGGGTCTCCCTACCCGGGGGGCGCCTTGGTGCCCGCCCCGCCGAGCCG | 420 |
| SEQ ID NO. 150 | Seq_2 | 361 | GGGCGGCAGCCTGGGGTCTCCCTACCCGGGGGGCGCCTTGGTGCCCGCCCCGCCGAGCCG | 420 |
| SEQ ID NO. 149 | | 421 | CTTCCTTGGAGCCTACGCCTACCCGCCGCGACCCCAGGCGGCCGGCTTCCCCGGCGCGGG | 480 |
| SEQ ID NO. 150 | Seq_2 | 421 | CTTCCTTGGAGCCTACGCCTACCCGCCGCGACCCCAGGCGGCCGGCTTCCCCGGCGCGGG | 480 |
| SEQ ID NO. 149 | | 481 | CGAGTCCTTCCCGCCGCCGCGGACGCCGAGGGCTACCAGCCGGGCGAGGGCTACGCCGC | 540 |
| SEQ ID NO. 150 | Seq_2 | 481 | CGAGTCCTTCCCGCCGCCGCGGACGCCGAGGGCTACCAGCCGGGCGAGGGCTACGCCGC | 540 |
| SEQ ID NO. 149 | | 541 | CCCGGACCCGCGCGCCGGGCTCTACCCGGGGCCGCGTGAGGACTACGCGCTACCCGCGGG | 600 |
| SEQ ID NO. 150 | Seq_2 | 541 | CCCGGACCCGCGCGCCGGGCTCTACCCGGGGCCGCGTGAGGACTACGCGCTACCCGCGGG | 600 |
| SEQ ID NO. 149 | | 601 | ACTGGAGGTGTCGGGGAAACTGAGGGTCGCGCTCAACAACCACCTGTTGTGGTCCAAGTT | 660 |
| SEQ ID NO. 150 | Seq_2 | 601 | ACTGGAGGTGTCGGGGAAACTGAGGGTCGCGCTCAACAACCACCTGTTGTGGTCCAAGTT | 660 |
| SEQ ID NO. 149 | | 661 | TAATCAGCACCAGACAGAGATGATCATCACCAAGCAGGGACGGCGGATGTTCCCATTCCT | 720 |
| SEQ ID NO. 150 | Seq_2 | 661 | TAATCAGCACCAGACAGAGATGATCATCACCAAGCAGGGACGGCGGATGTTCCCATTCCT | 720 |
| SEQ ID NO. 149 | | 721 | GTCATTTACTGTGGCCGGGCTGGAGCCCACCAGCCACTACAGGATGTTTGTGGACGTGGT | 780 |
| SEQ ID NO. 150 | Seq_2 | 721 | GTCATTTACTGTGGCCGGGCTGGAGCCCACCAGCCACTACAGGATGTTTGTGGACGTGGT | 780 |
| SEQ ID NO. 149 | | 781 | CTTGGTGGACCAGCACCACTGGCGGTACCAGAGCGGCAAGTGGGTGCAGTGTGGAAAGGC | 840 |
| SEQ ID NO. 150 | Seq_2 | 781 | CTTGGTGGACCAGCACCACTGGCGGTACCAGAGCGGCAAGTGGGTGCAGTGTGGAAAGGC | 840 |
| SEQ ID NO. 149 | | 841 | CGAGGGCAGCATGCCAGGAAACCGCCTGTACGTCCACCCGGACTCCCCCAACACAGGAGC | 900 |
| SEQ ID NO. 150 | Seq_2 | 841 | CGAGGGCAGCATGCCAGGAAACCGCCTGTACGTCCACCCGGACTCCCCCAACACAGGAGC | 900 |
| | | | | td54 |
| SEQ ID NO. 149 | | 901 | GCACTGGATGCGCCAGGAAGTTTCATTTGGGAAACTAAAGCTCACAAACAA␣␣␣␣␣␣␣␣␣ | 960 |
| SEQ ID NO. 150 | Seq_2 | 901 | GCACTGGATGCGCCAGGAAGTTTCATTTGGGAAACTAAAGCTCACAAACAACAAGGGGGC | 960 |
| SEQ ID NO. 149 | | 951 | ␣␣␣␣␣␣␣␣GTGACCCAGATGATTGTGCTCCAGTCCCTCCATAAGTACCAGCCCCGGCT | 1020 |
| SEQ ID NO. 150 | Seq_2 | 961 | GTCAACAATGTGACCCAGATGATTGTGCTCCAGTCCCTCCATAAGTACCAGCCCCGGCT | 1020 |
| SEQ ID NO. 149 | | 1021 | GCATATCGTTGAGGTGAACGACGGAGAGCCAGAGGCAGCCTGCAACGCTTCCAACACGCA | 1080 |
| SEQ ID NO. 150 | Seq_2 | 1021 | GCATATCGTTGAGGTGAACGACGGAGAGCCAGAGGCAGCCTGCAACGCTTCCAACACGCA | 1080 |
| | | | td69 td70 | |
| SEQ ID NO. 149 | | 1081 | TATCTTTACTTTCCA␣␣␣␣␣␣␣␣␣␣␣␣␣␣␣␣␣␣␣␣␣GTGACTGCCTACCAGAATGCCGAGAT | 1140 |
| SEQ ID NO. 150 | Seq_2 | 1081 | TATCTTTACTTTCCAAGAAACCCAGTTCATTGCCGTGACTGCCTACCAGAATGCCGAGAT | 1140 |
| SEQ ID NO. 149 | | 1141 | TACTCAGCTGAAAATTGATAATAACCCCTTTGCCAAAGGATTCCGGGAGAACTTTGAGTC | 1200 |
| SEQ ID NO. 150 | Seq_2 | 1141 | TACTCAGCTGAAAATTGATAATAACCCCTTTGCCAAAGGATTCCGGGAGAACTTTGAGTC | 1200 |
| SEQ ID NO. 149 | | 1201 | CATGTACACATCTGTTGACACCAGCATCCCCTCCCCGCCTGGACCCAACTGTCAATTCCT | 1260 |
| SEQ ID NO. 150 | Seq_2 | 1201 | CATGTACACATCTGTTGACACCAGCATCCCCTCCCCGCCTGGACCCAACTGTCAATTCCT | 1260 |
| SEQ ID NO. 149 | | 1261 | TGGGGAGATCACTACTCTCCTCTCCTACCCAACCAGTATCCTGTTCCCAGCCGCTTCTA | 1320 |
| SEQ ID NO. 150 | Seq_2 | 1261 | TGGGGAGATCACTACTCTCCTCTCCTACCCAACCAGTATCCTGTTCCCAGCCGCTTCTA | 1320 |
| SEQ ID NO. 149 | | 1321 | CCCCGACCTTCCTGGCCAGGCGAAGGATGTGGTTCCCCAGGCTTACTGGCTGGGGGCCCC | 1380 |
| SEQ ID NO. 150 | Seq_2 | 1321 | CCCCGACCTTCCTGGCCAGGCGAAGGATGTGGTTCCCCAGGCTTACTGGCTGGGGGCCCC | 1380 |
| SEQ ID NO. 149 | | 1381 | CCGGGACCACAGCTATG␣GGCTGAGTTTCGAGCAGTCAGCATGAAGCCTGCATTCTTGCC | 1440 |
| SEQ ID NO. 150t | Seq_2 | 1381 | CCGGGACCACAGCTATG␣GGCTGAGTTTCGAGCAGTCAGCATGAAGCCTGCATTCTTGCC | 1440 |

SEQ ID NO. 149

```
CGGCCCGCTGGAGAGGAAGCCCGAGAGCTGCCGCGCGCCTGCCGGACGAG
GGCGTAGAAGCCAGGCGTCAGAGCCCGGGCTCCGGTGGGGTCCCCCACCC
GGCCCTCGGGTCCCCCGCCCCCTGCTCCCTGCCCATCCCAGCCCACGCGA
CCCTCTCGCGCGCGGAGGGGCGGGTCCTCGACGGCTACGGGAAGGTGCCA
GCCCGCCCCGGATGGGCATCGTGGAGCCGGGTTGCGGAGACATGCTGACG
GGCACCGAGCCGATGCCGGGGAGCGACGAGGGCCGGGCGCCTGGCGCCGA
CCCGCAGCACCGCTACTTCTACCCGGAGCCGGGCGCGCAGGACGCGGACG
AGCGTCGCGGGGGCGGCAGCCTGGGGTCTCCCTACCCGGGGGCGCCTTG
GTGCCCGCCCCGCCGAGCCGCTTCCTTGGAGCCTACGCCTACCCGCCGCG
ACCCCAGGCGGCCGGCTTCCCCGGCGCGGGCGAGTCCTTCCCGCCGCCCG
CGGACGCCGAGGGCTACCAGCCGGGCGAGGGCTACGCCGCCCCGGACCCG
CGCGCCGGGCTCTACCCGGGGCCGCGTGAGGACTACGCGCTACCCGCGGG
ACTGGAGGTGTCGGGGAAACTGAGGGTCGCGCTCAACAACCACCTGTTGT
GGTCCAAGTTTAATCAGCACCAGACAGAGATGATCATCACCAAGCAGGGA
CGGCGGATGTTCCCATTCCTGTCATTTACTGTGGCCGGGCTGGAGCCCAC
CAGCCACTACAGGATGTTTGTGGACGTGGTCTTGGTGGACCAGCACCACT
GGCGGTACCAGAGCGGCAAGTGGGTGCAGTGTGGAAAGGCCGAGGGCAGC
ATGCCAGGAAACCGCCTGTACGTCCACCCGGACTCCCCCAACACAGGAGC
GCACTGGATGCGCCAGGAAGTTTCATTTGGGAAACTAAAGCTCACAAACA
ACAAGGGGCGTCCAACAATGTGACCCAGATGATTGTGCTCCAGTCCCTC
CATAAGTACCAGCCCCGGCTGCATATCGTTGAGGTGAACGACGGAGAGCC
AGAGGCAGCCTGCAACGCTTCCAACACGCATATCTTTACTTTCCAAGAAA
CCCAGTTCATTGCCGTGACTGCCTACCAGAATGCCGAGATTACTCAGCTG
AAAATTGATAATAACCCCTTTGCCAAAGGATTCCGGGAGAACTTTGAGTC
CATGTACACATCTGTTGACACCAGCATCCCCTCCCCGCCTGGACCCAACT
GTCAATTCCTTGGGGGAGATCACTACTCTCCTCTCCTACCCAACCACTAT
CCTGTTCCCAGCCGCTTCTACCCCGACCTTCCTGGCCAGGCGAAGGATGT
GCTTCCCCAGGCTTACTGGCTGGGGGCCCCCGGGACCACAGCTATGAGG
CTGACTTTCGAGCAGTCAGCATGAAGCCTGCATTCTTGCCCTCTGCCCCT
GGGCCCACCATGTCCTACTACCGAGGCCAGGAGGTCCTGGCACCTGGAGC
TGGCTGGCCTGTGGCACCCCAGTACCCTCCCAAGATGGGCCCGGCCAGCT
GCTTCCGCCCTATGCGGACTCTGCCCATGGAACCCGGCCCTGGAGGCTCA
GAGGGACGGGGACCAGAGGACCAGGGTCCCCCCTTGGTGTGGACTGAGAT
TGCCCCCATCCGGCCGGAATCCAGTGATTCAGGACTGGGCGAAGGAGACT
CTAAGAGGAGGCGCGTGTCCCCCTATCCTTCCAGTGGTGACAGCTCCTCC
CCTGCTGGGGCCCCTTCTCCTTTTGATAAGGAAGCTGAAGGACAGTTTTA
TAACTATTTTCCCAACTGAGCAGATGACATGATGAAAGGAACAGAAACAG
TGTTATTAGGTTGGAGGACACCGACTAATTTGGGAAACGCATGAAGGACT
GAGAAGGCCCCCGCTCCCTCTGGCCCTTCTCTGTTTAGTAGTTGGTTGGG
GAAGTGGGGCTCAAGAAGGATTTGGGGTTCACCAGATGCTTCCTGGCCC
ACGATGAAACCTGAGAGGGGTGTCCCCTTGCCCCATCCTCTGCCCTAACT
ACAGTCGTTTACCTGGTGCTGCGTCTTGCTTTTGGTTTCCAGCTGGAGAA
AAGAAGACAAGAAAGTCTTGGGCATGAAGGAGCTTTTTGCATCTAGTGGG
TGGGAGGGGTCAGGTGTGGGACATGGAGCAGGAGACTCCACTTTCTTCC
TTTGTACAGTAACTTTCAACCTTTTCGTTGGCATGTGTGTTAATCCCTGA
TCCAAAAAGAACAAATACACGTATGTTATAACCATCAGCCCGCCAGGGTC
AGGGAAAGGACTCACCTGACTTTGGACAGCTGGCCTGGGCTCCCCCTGCT
CAAACACAGTGGGGATCAGAGAAAAGGGGCTGGAAAGGGGGAATGGCCC
ACATCTCAAGAAGCAAGATATTGTTTGTGGTGGTTGTGTGTGGTGTGTG
TTTTTTCTTTTTCTTTCTTTTTATTTTTTTGAATGGGGGAGGCTATTTA
TTGTACTGAGAGTGGTGTCTGGATATATTCCTTTTGCTTCATCACTTTC
TGAAAATAAACATAAAACTGTTAAAAAAAAAAAAAAAAA
```

FIG. 4 A

```
                        SEQUENCE LISTING

<160> NUMBER OF SEQ ID NOS: 154

<210> SEQ ID NO 1
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd1 DNAzyme against GATA-3mRNA

<400> SEQUENCE: 1
tcggtcagag gctagctaca acgatgcgtt gct                              33

<210> SEQ ID NO 2
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hdg2 DNAzyme against GATA-3mRNA

<400> SEQUENCE: 2
ggcgtacgag gctagctaca acgactgctc ggt                              33

<210> SEQ ID NO 3
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd3 DNAzyme against GATA-3mRNA

<400> SEQUENCE: 3
ggcggcgtag gctagctaca acgagacctg ctc                              33

<210> SEQ ID NO 4
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd4 DNAzyme against GATA-3mRNA

<400> SEQUENCE: 4
ctcgggtcag gctagctaca acgactgggt agc                              33

<210> SEQ ID NO 5
<211> LENGTH: 33
<212> TYPE: DNA
<213> ORGANISM: Homo sapiens
<220> FEATURE:
<221> NAME/KEY: misc_feature
<222> LOCATION: (1)..(33)
```

<223> OTHER INFORMATION: hgd5 DNAzyme against GATA-3mRNA

<400> SEQUENCE: 5
tcctctgcag gctagctaca acgacggggt cct    33

<210> SEQ ID NO 6
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd6 DNAzyme against GATA-3mRNA

<400> SEQUENCE: 6
actctgcaag gctagctaca acgatctgcg agc    33

<210> SEQ ID NO 7
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd7 DNAzyme against GATA-3mRNA

<400> SEQUENCE: 7
gggcgacgag gctagctaca acgatctgca att    33

<210> SEQ ID NO 8
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd8 DNAzyme against GATA-3mRNA

<400> SEQUENCE: 8
aaggggcgag gctagctaca acgagactct gca    33

<210> SEQ ID NO 9
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd9 DNAzyme against GATA-3mRNA

<400> SEQUENCE: 9
aaaacgggag gctagctaca acgacaggtt gta    33

<210> SEQ ID NO 10
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd10 DNAzyme against GATA-3mRNA

<400> SEQUENCE: 10
agaataaaag gctagctaca acgagggacc agg    33

<210> SEQ ID NO 11
<211> LENGTH: 33
<212> TYPE: DNA

```
<213> ORGANISM: Homo sapiens
<220> FEATURE:
<221> NAME/KEY: misc_feature
<222> LOCATION: (1)..(33)
<223> OTHER INFORMATION: hgd11 DNAzyme against GATA-3mRNA

<400> SEQUENCE: 11
atggcagaag gctagctaca acgaaaaacg gga                                33

<210> SEQ ID NO 12
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd12 DNAzyme against GATA-3mRNA

<400> SEQUENCE: 12
aactgggtag gctagctaca acgaggcaga ata                                33

<210> SEQ ID NO 13
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd13 DNAzyme against GATA-3mRNA

<400> SEQUENCE: 13
atccaaaaag gctagctaca acgatgggta tgg                                33

<210> SEQ ID NO 14
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd14 DNAzyme against GATA-3mRNA

<400> SEQUENCE: 14
aggggaagag gctagctaca acgaaaaaat cca                                33

<210> SEQ ID NO 15
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd15 DNAzyme against GATA-3mRNA

<400> SEQUENCE: 15
ttttaaaaag gctagctaca acgatatctt gga                                33

<210> SEQ ID NO 16
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd16 DNAzyme against GATA-3mRNA

<400> SEQUENCE: 16 gtgggggag gctagctaca acgagggaag gct                                 33
```

```
<210> SEQ ID NO 17
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd17 DNAzyme against GATA-3mRNA

<400> SEQUENCE: 17
gttgaatgag gctagctaca acgattgctt tcg                                33

<210> SEQ ID NO 18
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd18 DNAzyme against GATA-3mRNA

<400> SEQUENCE: 18
gtcgttgaag gctagctaca acgagatttg ctt                                33

<210> SEQ ID NO 19
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd19 DNAzyme against GATA-3mRNA

<400> SEQUENCE: 19
ggcccggaag gctagctaca acgaccgcgc gcg                                33

<210> SEQ ID NO 20
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd20 DNAzyme against GATA-3mRNA

<400> SEQUENCE: 20
tcacctccag gctagctaca acgaggcctc ggc                                33

<210> SEQ ID NO 21
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd21 DNAzyme against GATA-3mRNA

<400> SEQUENCE: 21
ccgccgtcag gctagctaca acgactccat ggc                                33

<210> SEQ ID NO 22
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd22 DNAzyme against GATA-3mRNA
```

```
<400> SEQUENCE: 22
ggtggctcag gctagctaca acgaccagcg cgg                            33

<210> SEQ ID NO 23
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd23 DNAzyme against GATA-3mRNA

<400> SEQUENCE: 23
cgttgagcag gctagctaca acgaggcggg gtg                            33

<210> SEQ ID NO 24
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd24 DNAzyme against GATA-3mRNA

<400> SEQUENCE: 24
ccgcgtccag gctagctaca acgagtagga gtg                            33

<210> SEQ ID NO 25
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd25 DNAzyme against GATA-3mRNA

<400> SEQUENCE: 25
cagcgggtag gctagctaca acgatgcgcc gcg                            33

<210> SEQ ID NO 26
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd26 DNAzyme against GATA-3mRNA

<400> SEQUENCE: 26
gcacatccag gctagctaca acgactcctc cgg                            33

<210> SEQ ID NO 27
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd27 DNAzyme against GATA-3mRNA

<400> SEQUENCE: 27
aaaagcacag gctagctaca acgaccacct cct                            33

<210> SEQ ID NO 28
<211> LENGTH: 33
<212> TYPE: DNA
<213> ORGANISM: Homo sapiens
<220> FEATURE:
```

```
<221> NAME/KEY: misc_feature
<222> LOCATION: (1)..(33)
<223> OTHER INFORMATION: hgd28 DNAzyme against GATA-3mRNA

<400> SEQUENCE: 28
taaaaagcag gctagctaca acgaatccac ctc                                   33

<210> SEQ ID NO 29
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd29 DNAzyme against GATA-3mRNA

<400> SEQUENCE: 29
gaccgtcgag gctagctaca acgagttaaa aag                                   33

<210> SEQ ID NO 30
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd30 DNAzyme against GATA-3mRNA

<400> SEQUENCE: 30
ttgccttgag gctagctaca acgacgtcga tgt                                   33

<210> SEQ ID NO 31
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd31 DNAzyme against GATA-3mRNA

<400> SEQUENCE: 31
agggcgggag gctagctaca acgagtggtt gcc                                   33

<210> SEQ ID NO 32
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd32 DNAzyme against GATA-3mRNA

<400> SEQUENCE: 32
tggccctgag gctagctaca acgacgagtt tcc                                   33

<210> SEQ ID NO 33
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd33 DNAzyme against GATA-3mRNA

<400> SEQUENCE: 33
acctctgcag gctagctaca acgacgtggc cct                                   33

<210> SEQ ID NO 34
```

```
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd34 DNAzyme against GATA-3mRNA

<400> SEQUENCE: 34
cggagggtag gctagctaca acgactctgc acc                                  33

<210> SEQ ID NO 35
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd35 DNAzyme against GATA-3mRNA

<400> SEQUENCE: 35
ggcggcacag gctagctaca acgactggct ccc                                  33

<210> SEQ ID NO 36
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd36 DNAzyme against GATA-3mRNA

<400> SEQUENCE: 36
cgggcggcag gctagctaca acgaacctgg ctc                                  33

<210> SEQ ID NO 37
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd37 DNAzyme against GATA-3mRNA

<400> SEQUENCE: 37
agggatccag gctagctaca acgagaagca gag                                  33

<210> SEQ ID NO 38
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd38 DNAzyme against GATA-3mRNA

<400> SEQUENCE: 38
gggtagggag gctagctaca acgaccatga agc                                  33

<210> SEQ ID NO 39
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd39 DNAzyme against GATA-3mRNA

<400> SEQUENCE: 39
```
gggctgagag gctagctaca acgatccagg ggg             33

<210> SEQ ID NO 40
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd40 DNAzyme against GATA-3mRNA

<400> SEQUENCE: 40
gtggatggag gctagctaca acgagtcttg gag             33

<210> SEQ ID NO 41
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd 41 DNAzyme against GATA-3mRNA

<400> SEQUENCE: 41
cgtggtggag gctagctaca acgaggacgt ctt             33

<210> SEQ ID NO 42
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd 42 DNAzyme against GATA-3mRNA

<400> SEQUENCE: 42
gggggtagag gctagctaca acgaggagag ggg             33

<210> SEQ ID NO 43
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd 43 DNAzyme against GATA-3mRNA

<400> SEQUENCE: 43
ggaggaggag gctagctaca acgagaggcc ggg             33

<210> SEQ ID NO 44
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd44 DNAzyme against GATA-3mRNA

<400> SEQUENCE: 44
gccccccgag gctagctaca acgaaaggag gag             33

<210> SEQ ID NO 45
<211> LENGTH: 33
<212> TYPE: DNA
<213> ORGANISM: Homo sapiens
<220> FEATURE:
<221> NAME/KEY: misc_feature
<222> LOCATION: (1)..(33)

<223> OTHER INFORMATION: hgd45 DNAzyme against GATA-3mRNA

<400> SEQUENCE: 45
ccggggagag gctagctaca acgagtcctt cgg    33

<210> SEQ ID NO 46
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd46 DNAzyme against GATA-3mRNA

<400> SEQUENCE: 46
ggacagcgag gctagctaca acgagggtcc ggg    33

<210> SEQ ID NO 47
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd47 DNAzyme against GATA-3mRNA

<400> SEQUENCE: 47
tggggtggag gctagctaca acgaagcgat ggg    33

<210> SEQ ID NO 48
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd48 DNAzyme against GATA-3mRNA

<400> SEQUENCE: 48
cttgaggcag gctagctaca acgatctttc tcg    33

<210> SEQ ID NO 49
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd49 DNAzyme against GATA-3mRNA

<400> SEQUENCE: 49
cacctggtag gctagctaca acgattgagg cac    33

<210> SEQ ID NO 50
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd50 DNAzyme against GATA-3mRNA

<400> SEQUENCE: 50
gcaggggcag gctagctaca acgactggta ctt    33

<210> SEQ ID NO 51
<211> LENGTH: 33
<212> TYPE: DNA

```
<213> ORGANISM: Homo sapiens
<220> FEATURE:
<221> NAME/KEY: misc_feature
<222> LOCATION: (1)..(33)
<223> OTHER INFORMATION: hgd51 DNAzyme against GATA-3mRNA

<400> SEQUENCE: 51
ccagcttcag gctagctaca acgagctgtc ggg                          33

<210> SEQ ID NO 52
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd52 DNAzyme against GATA-3mRNA

<400> SEQUENCE: 52
gtgggacgag gctagctaca acgatccagc ttc                          33

<210> SEQ ID NO 53
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd53 DNAzyme against GATA-3mRNA

<400> SEQUENCE: 53
ggagtgggag gctagctaca acgagactcc agc                          33

<210> SEQ ID NO 54
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd54 DNAzyme against GATA-3mRNA

<400> SEQUENCE: 54
atgctgccag gctagctaca acgagggagt ggg                          33

<210> SEQ ID NO 55
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd55 DNAzyme against GATA-3mRNA

<400> SEQUENCE: 55
gggcggtcag gctagctaca acgagctgcc acg                          33

<210> SEQ ID NO 56
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd56 DNAzyme against GATA-3mRNA

<400> SEQUENCE: 56
gaggctccag gctagctaca acgaccaggg cgg                          33
```

```
<210> SEQ ID NO 57
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd57 DNAzyme against GATA-3mRNA

<400> SEQUENCE: 57
gtgggtcgag gctagctaca acgagaggag gct                               33

<210> SEQ ID NO 58
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd58 DNAzyme against GATA-3mRNA

<400> SEQUENCE: 58
aggtggtgag gctagctaca acgaggggtg gtg                               33

<210> SEQ ID NO 59
<211> LENGTH: 33
<212> TYPE: DNA
<213> ORGANISM: Homo sapiens
<220> FEATURE:
<221> NAME/KEY: Misc_feature
<222> LOCATION: (1)..(33)
<223> OTHER INFORMATION: hgd59 DNAzyme against GATA-3mRNA

<400> SEQUENCE: 59
actcgggcag gctagctaca acgagtaggg cgg                               33

<210> SEQ ID NO 60
<211> LENGTH: 33
<212> TYPE: DNA
<213> ORGANISM: Homo sapiens
<220> FEATURE:
<221> NAME/KEY: misc_feature
<222> LOCATION: (1)..(33)
      <223  >hgd60 DNAzyme against GATA-3mRNA

<400> SEQUENCE: 60
ggagctgtag gctagctaca acgatcgggc acg                               33

<210> SEQ ID NO 61
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd61 DNAzyme against GATA-3mRNA

<400> SEQUENCE: 61
ggacttgcag gctagctaca acgaccgaag ccg                               33

<210> SEQ ID NO 62
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd62 DNAzyme against GATA-3mRNA
```

```
<400> SEQUENCE: 62
gggcctggag gctagctaca acgattgcat ccg                                    33

<210> SEQ ID NO 63
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd63 DNAzyme against GATA-3mRNA

<400> SEQUENCE: 63
tgtgctggag gctagctaca acgacgggcc ttg                                    33

<210> SEQ ID NO 64
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd64 DNAzyme against GATA-3mRNA

<400> SEQUENCE: 64
gttcacacag gctagctaca acgatccctg cct                                    33

<210> SEQ ID NO 65
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd65 DNAzyme against GATA-3mRNA

<400> SEQUENCE: 65
cagttcacag gctagctaca acgaactccc tgc                                    33

<210> SEQ ID NO 66
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd66 DNAzyme against GATA-3mRNA

<400> SEQUENCE: 66
cacagttcag gctagctaca acgaacactc cct                                    33

<210> SEQ ID NO 67
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd67 DNAzyme against GATA-3mRNA

<400> SEQUENCE: 67
gttgccccag gctagctaca acgaagttca cac                                    33

<210> SEQ ID NO 68
<211> LENGTH: 33
<212> TYPE: DNA
<213> ORGANISM: Homo sapiens
<220> FEATURE:
```

```
<221> NAME/KEY: misc_feature
<222> LOCATION: (1)..(33)
<223> OTHER INFORMATION: hgd68 DNAzyme against GATA-3mRNA

<400> SEQUENCE: 68
tcgccgccag gctagctaca acgaagtggg gtc                            33

<210> SEQ ID NO 69
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd69 DNAzyme against GATA-3mRNA

<400> SEQUENCE: 69
cccgtgccag gctagctaca acgactcgcc gcc                            33

<210> SEQ ID NO 70
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hgd70 DNAzyme against GATA-3mRNA

<400> SEQUENCE: 70
ggcgttgcag gctagctaca acgaaggtag tgt                            33

<210> SEQ ID NO 71
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td1 DNAzyme against T-bet mRNA

<400> SEQUENCE: 71
tggcttctag gctagctaca acgagccctc gtc                            33

<210> SEQ ID NO 72
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td2 DNAzyme against T-bet mRNA

<400> SEQUENCE: 72
gggctctgag gctagctaca acgagcctgg ctt                            33

<210> SEQ ID NO 73
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td3 DNAzyme against T-bet mRNA

<400> SEQUENCE: 73
gggaccccag gctagctaca acgacggagc ccg                            33

<210> SEQ ID NO 74
```

```
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td4 DNAzyme against T-bet mRNA

<400> SEQUENCE: 74
ggtgggggag gctagctaca acgacccacc gga                                33

<210> SEQ ID NO 75
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td5 DNAzyme against T-bet mRNA

<400> SEQUENCE: 75 ggcggggag gctagctaca acgaccgagg gcc                                 33

<210> SEQ ID NO 76
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td6 DNAzyme against T-bet mRNA

<400> SEQUENCE: 76
gggctgggag gctagctaca acgagggcag gga                                33

<210> SEQ ID NO 77
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td7 DNAzyme against T-bet mRNA

<400> SEQUENCE: 77
cgtcgaggag gctagctaca acgaccgccc ctc                                33

<210> SEQ ID NO 78
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td8 DNAzyme against T-bet mRNA

<400> SEQUENCE: 78
gggctggcag gctagctaca acgacttccc gta                                33

<210> SEQ ID NO 79
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td9 DNAzyme against T-bet mRNA

<400> SEQUENCE: 79
```
cgatgcccag gctagctaca acgaccgggg cgg                                33

<210> SEQ ID NO 80
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td10 DNAzyme against T-bet mRNA

<400> SEQUENCE: 80
gctccacgag gctagctaca acgagcccat ccg                                33

<210> SEQ ID NO 81
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td11 DNAzyme against T-bet mRNA

<400> SEQUENCE: 81
ccggctccag gctagctaca acgagatgcc cat                                33

<210> SEQ ID NO 82
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td12 DNAzyme against T-bet mRNA

<400> SEQUENCE: 82
tctccgcaag gctagctaca acgaccggct cca                                33

<210> SEQ ID NO 83
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td13 DNAzyme against T-bet mRNA

<400> SEQUENCE: 83
ccgtcagcag gctagctaca acgagtctcc gca                                33

<210> SEQ ID NO 84
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td14 DNAzyme against T-bet mRNA

<400> SEQUENCE: 84
tccccggcag gctagctaca acgacggctc ggt                                33

<210> SEQ ID NO 85
<211> LENGTH: 33
<212> TYPE: DNA
<213> ORGANISM: Homo sapiens
<220> FEATURE:
<221> NAME/KEY: misc_feature
<222> LOCATION: (1)..(33)

```
<223> OTHER INFORMATION: td15 DNAzyme against T-bet mRNA

<400> SEQUENCE: 85
cccccgcgag gctagctaca acgagctcgt ccg                                    33

<210> SEQ ID NO 86
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td16 DNAzyme against T-bet mRNA

<400> SEQUENCE: 86
gtagggagag gctagctaca acgacccagg ctg                                    33

<210> SEQ ID NO 87
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td17 DNAzyme against T-bet mRNA

<400> SEQUENCE: 87
gggcgggcag gctagctaca acgacaaggc gcc                                    33

<210> SEQ ID NO 88
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td18 DNAzyme against T-bet mRNA

<400> SEQUENCE: 88
cgggaaggag gctagctaca acgatcgccc gcg                                    33

<210> SEQ ID NO 89
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td19 DNAzyme against T-bet mRNA

<400> SEQUENCE: 89
tagtcctcag gctagctaca acgagcggcc ccg                                    33

<210> SEQ ID NO 90
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td20 DNAzyme against T-bet mRNA

<400> SEQUENCE: 90
tccccgacag gctagctaca acgactccag tcc                                    33

<210> SEQ ID NO 91
<211> LENGTH: 33
<212> TYPE: DNA
```

```
<213> ORGANISM: Homo sapiens
<220> FEATURE:
<221> NAME/KEY: misc_feature
<222> LOCATION: (1)..(33)
<223> OTHER INFORMATION: td21 DNAzyme against T-bet mRNA

<400> SEQUENCE: 91
tttccccgag gctagctaca acgaacctcc agt                              33

<210> SEQ ID NO 92
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td22 DNAzyme against T-bet mRNA

<400> SEQUENCE: 92
tgagcgcgag gctagctaca acgacctcag ttt                              33

<210> SEQ ID NO 93
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td23 DNAzyme against T-bet mRNA

<400> SEQUENCE: 93
ggaccacaag gctagctaca acgaaggtgg ttg                              33

<210> SEQ ID NO 94
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td24 DNAzyme against T-bet mRNA

<400> SEQUENCE: 94
cttggaccag gctagctaca acgaaacagg tgg                              33

<210> SEQ ID NO 95
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td25 DNAzyme against T-bet mRNA

<400> SEQUENCE: 95
aaacttggag gctagctaca acgacacaac agg                              33

<210> SEQ ID NO 96
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td26 DNAzyme against T-bet mRNA

<400> SEQUENCE: 96
ctgattaaag gctagctaca acgattggac cac                              33
```

```
<210> SEQ ID NO 97
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td27 DNAzyme against T-bet mRNA

<400> SEQUENCE: 97
tggtgctgag gctagctaca acgataaact tgg                                    33

<210> SEQ ID NO 98
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td28 DNAzyme against T-bet mRNA

<400> SEQUENCE: 98
tgatgatcag gctagctaca acgactctgt ctg                                    33

<210> SEQ ID NO 99
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td29 DNAzyme against T-bet mRNA

<400> SEQUENCE: 99
tggtgatgag gctagctaca acgacatctc tgt                                    33

<210> SEQ ID NO 100
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td30 DNAzyme against T-bet mRNA

<400> SEQUENCE: 100
gcttggtgag gctagctaca acgagatcat ctc                                    33

<210> SEQ ID NO 101
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td31 DNAzyme against T-bet mRNA

<400> SEQUENCE: 101
atgggaacag gctagctaca acgaccgccg tcc                                    33

<210> SEQ ID NO 102
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td32 DNAzyme against T-bet mRNA
```

```
<400> SEQUENCE: 102
gaatgggaag gctagctaca acgaatccgc cgt                              33

<210> SEQ ID NO 103
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td33 DNAzyme against T-bet mRNA

<400> SEQUENCE: 103
tgacaggaag gctagctaca acgagggaac atc                              33

<210> SEQ ID NO 104
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td34 DNAzyme against T-bet mRNA

<400> SEQUENCE: 104
agtaaatgag gctagctaca acgaaggaat ggg                              33

<210> SEQ ID NO 105
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td35 DNAzyme against T-bet mRNA

<400> SEQUENCE: 105
cacagtaaag gctagctaca acgagacagg aat                              33

<210> SEQ ID NO 106
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td36 DNAzyme against T-bet mRNA

<400> SEQUENCE: 106
gcccggccag gctagctaca acgaagtaaa tga                              33

<210> SEQ ID NO 107
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td37 DNAzyme against T-bet mRNA

<400> SEQUENCE: 107
ccacaaacag gctagctaca acgacctgta gtg                              33

<210> SEQ ID NO 108
<211> LENGTH: 33
<212> TYPE: DNA
<213> ORGANISM: Homo sapiens
<220> FEATURE:
```

```
<221> NAME/KEY: misc_feature
<222> LOCATION: (1)..(33)
<223> OTHER INFORMATION: td38 DNAzyme against T-bet mRNA

<400> SEQUENCE: 108
gtccacaaag gctagctaca acgaatcctg tag                                33

<210> SEQ ID NO 109
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td39 DNAzyme against T-bet mRNA

<400> SEQUENCE: 109
ccacgtccag gctagctaca acgaaaacat cct                                33

<210> SEQ ID NO 110
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td40 DNAzyme against T-bet mRNA

<400> SEQUENCE: 110
ccaagaccag gctagctaca acgagtccac aaa                                33

<210> SEQ ID NO 111
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td41 DNAzyme against T-bet mRNA

<400> SEQUENCE: 111
ccaccaagag gctagctaca acgacacgtc cac                                33

<210> SEQ ID NO 112
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td42 DNAzyme against T-bet mRNA

<400> SEQUENCE: 112
gctggtccag gctagctaca acgacaagac cac                                33

<210> SEQ ID NO 113
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td43 DNAzyme against T-bet mRNA

<400> SEQUENCE: 113
gctctggtag gctagctaca acgacgccag tgg                                33

<210> SEQ ID NO 114
```

```
<210> SEQ ID NO 114
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td44 DNAzyme against T-bet mRNA

<400> SEQUENCE: 114
ctgcacccag gctagctaca acgattgccg ctc                                    33

<210> SEQ ID NO 115
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td45 DNAzyme against T-bet mRNA

<400> SEQUENCE: 115
cacactgcag gctagctaca acgaccactt gcc                                    33

<210> SEQ ID NO 116
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td46 DNAzyme against T-bet mRNA

<400> SEQUENCE: 116
ctttccacag gctagctaca acgatgcacc cac                                    33

<210> SEQ ID NO 117
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td47 DNAzyme against T-bet mRNA

<400> SEQUENCE: 117
gcctttccag gctagctaca acgaactgca ccc                                    33

<210> SEQ ID NO 118
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td48 DNAzyme against T-bet mRNA

<400> SEQUENCE: 118
ttcctggcag gctagctaca acgagctgcc ctc                                    33

<210> SEQ ID NO 119
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td49 DNAzyme against T-bet mRNA

<400> SEQUENCE: 119
```
gtggacgtag gctagctaca acgaaggcgg ttt                                          33

<210> SEQ ID NO 120
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td50 DNAzyme against T-bet mRNA

<400> SEQUENCE: 120
ccgggtggag gctagctaca acgagtacag gcg                                          33

<210> SEQ ID NO 121
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td51 DNAzyme against T-bet mRNA

<400> SEQUENCE: 121
cctggcgcag gctagctaca acgaccagtg cgc                                          33

<210> SEQ ID NO 122
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td52 DNAzyme against T-bet mRNA

<400> SEQUENCE: 122
caaatgaaag gctagctaca acgattcctg gcg                                          33

<210> SEQ ID NO 123
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td53 DNAzyme against T-bet mRNA

<400> SEQUENCE: 123
tttcccaaag gctagctaca acgagaaact tcc                                          33

<210> SEQ ID NO 124
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td54 DNAzyme against T-bet mRNA

<400> SEQUENCE: 124
attgttggag gctagctaca acgagccccc ttg                                          33

<210> SEQ ID NO 125
<211> LENGTH: 33
<212> TYPE: DNA
<213> ORGANISM: Homo sapiens
<220> FEATURE:
<221> NAME/KEY: misc_feature
<222> LOCATION: (1)..(33)

<223> OTHER INFORMATION: td55 DNAzyme against T-bet mRNA

<400> SEQUENCE: 125
tgggtcacag gctagctaca acgatgttgg acg					33

<210> SEQ ID NO 126
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td56 DNAzyme against T-bet mRNA

<400> SEQUENCE: 126
tctgggtcag gctagctaca acgaattgtt gga					33

<210> SEQ ID NO 127
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td57 DNAzyme against T-bet mRNA

<400> SEQUENCE: 127
gcacaatcag gctagctaca acgactgggt cac					33

<210> SEQ ID NO 128
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td58 DNAzyme against T-bet mRNA

<400> SEQUENCE: 128
ggagcacaag gctagctaca acgacatctg ggt					33

<210> SEQ ID NO 129
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td59 DNAzyme against T-bet mRNA

<400> SEQUENCE: 129
actggagcag gctagctaca acgaaatcat ctg					33

<210> SEQ ID NO 130
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td60 DNAzyme against T-bet mRNA

<400> SEQUENCE: 130
atggagggag gctagctaca acgatggagc aca					33

<210> SEQ ID NO 131
<211> LENGTH: 33
<212> TYPE: DNA

```
<213> ORGANISM: Homo sapiens
<220> FEATURE:
<221> NAME/KEY: misc_feature
<222> LOCATION: (1)..(33)
<223> OTHER INFORMATION: td61 DNAzyme against T-bet mRNA

<400> SEQUENCE: 131
tggtacttag gctagctaca acgaggaggg act                              33

<210> SEQ ID NO 132
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td62 DNAzyme against T-bet mRNA

<400> SEQUENCE: 132
gggctggtag gctagctaca acgattatgg agg                              33

<210> SEQ ID NO 133
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td63 DNAzyme against T-bet mRNA

<400> SEQUENCE: 133
tcaacgatag gctagctaca acgagcagcc ggg                              33

<210> SEQ ID NO 134
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td64 DNAzyme against T-bet mRNA

<400> SEQUENCE: 134
cctcaacgag gctagctaca acgaatgcag ccg                              33

<210> SEQ ID NO 135
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td65 DNAzyme against T-bet mRNA

<400> SEQUENCE: 135
tcacctcaag gctagctaca acgagatatg cag                              33

<210> SEQ ID NO 136
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td66 DNAzyme against T-bet mRNA

<400> SEQUENCE: 136
cgtcgttcag gctagctaca acgactcaac gat                              33
```

<210> SEQ ID NO 137
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td67 DNAzyme against T-bet mRNA

<400> SEQUENCE: 137
gtaaagatag gctagctaca acgagcgtgt tgg                                33

<210> SEQ ID NO 138
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td68 DNAzyme against T-bet mRNA

<400> SEQUENCE: 138
aagtaaagag gctagctaca acgaatgcgt gtt                                33

<210> SEQ ID NO 139
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td69 DNAzyme against T-bet mRNA

<400> SEQUENCE: 139
ggcaatgaag gctagctaca acgatgggtt tct                                33

<210> SEQ ID NO 140
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td70 DNAzyme against T-bet mRNA

<400> SEQUENCE: 140
tcacggcaag gctagctaca acgagaactg ggt                                33

<210> SEQ ID NO 141
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td71 DNAzyme against T-bet mRNA

<400> SEQUENCE: 141
aggcagtcag gctagctaca acgaggcaat gaa                                33

<210> SEQ ID NO 142
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td72 DNAzyme against T-bet mRNA

<400> SEQUENCE: 142
atctcggcag gctagctaca acgatctggt agg                                    33

<210> SEQ ID NO 143
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td73 DNAzyme against T-bet mRNA

<400> SEQUENCE: 143
gctgagtaag gctagctaca acgactcggc att                                    33

<210> SEQ ID NO 144
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td74 DNAzyme against T-bet mRNA

<400> SEQUENCE: 144
tattatcaag gctagctaca acgatttcag ctg                                    33

<210> SEQ ID NO 145
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td75 DNAzyme against T-bet mRNA

<400> SEQUENCE: 145
gggttattag gctagctaca acgacaattt tca                                    33

<210> SEQ ID NO 146
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td76 DNAzyme against T-bet mRNA

<400> SEQUENCE: 146
aaggggttag gctagctaca acgatatcaa ttt                                    33

<210> SEQ ID NO 147
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: td77 DNAzyme against T-bet mRNA

<400> SEQUENCE: 147
ctcccggaag gctagctaca acgaccttrg gca                                    33

<210> SEQ ID NO 148
<211> LENGTH: 33
<212> TYPE: DNA
<213> ORGANISM: Homo sapiens
<220> FEATURE:

```
<221> NAME/KEY: misc_feature
<222> LOCATION: (1)..(33)
<223> OTHER INFORMATION: td78 DNAzyme against T-bet mRNA

<400> SEQUENCE: 148
gtacatggag gctagctaca acgatcaaag ttc                                    33

<210> SEQ ID NO 149
<211> LENGTH: 2588
<212> TYPE: DNA
<213> ORGANISM: Homo sapiens
<220> FEATURE:
<221> NAME/KEY: td54 bindingsite
<222> LOCATION: (952)..(970)
<220> FEATURE:
<221> NAME/KEY: td69 bindingsite
<222> LOCATION: (1096)..(1114)
<220> FEATURE:
<221> NAME/KEY: td70 bindingsite
<222> LOCATION: (1100)..(1118)

<400> SEQUENCE: 149
cggcccgctg gagaggaagc ccgagagctg ccgcgcgcct gccggacgag ggcgtagaag       60
ccaggcgtca gagcccgggc tccggtgggg tcccccaccc ggccctcggg tccccgcccc      120
cctgctccct gcccatccca gcccacgcga ccctctcgcg cgcggagggg cgggtcctcg      180
acggctacgg gaaggtgcca gcccgccccg gatgggcatc gtggagccgg gttgcgcgaga     240 catgctgacg ggcaccgagc cgatgccggg gagcgacgag ggccgggcgc ctggcgccga     300
cccgcagcac cgctacttct acccggagcc gggcgcgcag gacgcggacg agcgtcgcgg     360
gggcggcagc ctggggtctc cctacccggg gggcgccttg gtgcccgccc cgccgagccg     420
cttccttgga gcctacgcct acccgccgcg accccaggcg gccggcttcc ccggcgcggg     480
cgagtccttc ccgccgcccg cggacgccga gggctaccag ccgggcgagg gctacgccgc     540
cccggacccg cgcgccggc tctacccggg gccgcgtgag gactacgcgc tacccgcggg      600
actggaggtg tcggggaaac tgagggtcgc gctcaacaac cacctgttgt ggtccaagtt     660
taatcagcac cagacagaga tgatcatcac caagcaggga cggcggatgt tcccattcct     720
gtcatttact gtggccgggc tggagcccac cagccactac aggatgtttg tggacgtggt     780
cttggtggac cagcaccact ggcggtacca gagcggcaag tgggtgcagt gtggaaaggc     840
cgagggcagc atgccaggaa accgcctgta cgtccacccg gactccccca acacaggagc     900
gcactggatg cgccaggaag tttcatttgg gaaactaaag ctcacaaaca caaggggggc    960
gtccaacaat gtgacccaga tgattgtgct ccagtccctc cataagtacc agccccggct    1020
gcatatcgtt gaggtgaacg acggagagcc agaggcagcc tgcaacgctt ccaacacgca    1080
tatctttact ttccaagaaa cccagttcat tgccgtgact gcctaccaga atgccgagat    1140
tactcagctg aaaattgata taaaccccctt tgccaaagga ttccgggaga actttgagtc    1200
catgtacaca tctgttgaca ccagcatccc ctcccgcct ggacccaact gtcaattcct     1260
tgggggagat cactactctc ctctcctacc caaccagtat cctgttccca gccgcttcta    1320
ccccgacctt cctggccagg cgaaggatgt ggttccccag gcttactggc tgggggcccc    1380
ccgggaccac agctatgagg ctgagtttcg agcagtcagc atgaagcctg cattcttgcc    1440 ctctgccccct gggcccacca gtcctacta ccgaggccca gaggtcctgg cacctggagc    1500
tggctggcct gtggcacccc agtaccctcc caagatgggc ccggccagct ggttccgccc    1560
tatgcggact ctgcccatgg aacccggccc tggaggctca gagggacggg gaccagagga    1620 ccaggggtccc cccttggtgt ggactgagat tgccccccatc cggccggaat ccagtgattc    1680
```

-continued

```
aggactgggc gaaggagact ctaagaggag gcgcgtgtcc ccctatcctt ccagtggtga    1740
cagctcctcc cctgctgggg cccccttctcc ttttgataag gaagctgaag gacagtttta    1800
taactatttt cccaactgag cagatgacat gatgaaagga acagaaacag tgttattagg    1860
ttggaggaca ccgactaatt tgggaaacgg atgaaggact gagaaggccc ccgctccctc    1920
tggcccttct ctgtttagta gttggttggg gaagtgggc tcaagaagga ttttggggtt    1980
caccagatgc ttcctggccc acgatgaaac ctgagagggg tgtccccttg ccccatcctc    2040
tgccctaact acagtcgttt acctggtgct gcgtcttgct tttggtttcc agctggagaa    2100
aagaagacaa gaaagtcttg ggcatgaagg agcttttgc atctagtggg tgggagggt    2160 caggtgtggg acatgggagc aggagactcc actttcttcc tttgtacagt aactttcaac    2220
cttttcgttg gcatgtgtgt taatccctga tccaaaaaga acaaatacac gtatgttata    2280
accatcagcc cgccagggtc agggaaagga ctcacctgac tttggacagc tggcctgggc    2340 tcccccctgct caaacacagt ggggatcaga gaaaagggga tggaagggg ggaatggccc    2400 acatctcaag aagcaagata ttgtttgtgg tggttgtgtg tgggtgtgtg ttttttcttt    2460
ttctttcttt ttattttttt tgaatggggg aggctattta ttgtactgag agtggtgtct    2520
ggatatattc cttttgtctt catcactttc tgaaataaac ataaaactgt taaaaaaaa    2580 aaaaaaaa                                                              2588
```

<210> SEQ ID NO 150
<211> LENGTH: 2450
<212> TYPE: DNA
<213> ORGANISM: Homo sapiens
<220> FEATURE:
<221> NAME/KEY: mutation
<222> LOCATION: (134)..(134)
<220> FEATURE:
<221> NAME/KEY: mutation
<222> LOCATION: (310)..(310)
<220> FEATURE:
<221> NAME/KEY: td54 bindingsite
<222> LOCATION: (952)..(970)
<220> FEATURE:
<221> NAME/KEY: td69 bindingsite
<222> LOCATION: (1096)..(1114)
<220> FEATURE:
<221> NAME/KEY: td70 bindingsite
<222> LOCATION: (1100)..(1118)
<220> FEATURE:
<221> NAME/KEY: mutation
<222> LOCATION: (1399)..(1399)
<220> FEATURE:
<221> NAME/KEY: mutation
<222> LOCATION: (1556)..(1556)

<400> SEQUENCE: 150

```
cggcccgctg gagaggaagc ccgagagctg ccgcgcgcct gccggacgag ggcgtagaag     60
ccaggcgtca gagcccgggc tccggtgggg tccccaccc ggccctcggg tccccgccc    120 cctgctccct gcctatccca gcccacgcga ccctctcgcg cgcggagggg cgggtcctcg    180
acggctacgg gaaggtgcca gcccgccccg gatgggcatc gtggagccgg gttgcggaga    240
catgctgacg ggcaccgagc cgatgccggg gagcgacgag ggccgggcgc ctggcgccga    300
cccgcagcag cgctacttct acccggagcc gggcgcgcag gacgcggacg agcgtcgcgg    360
gggcggcagc ctggggtctc cctacccggg gggcgccttg gtgcccgccc cgccgagccg    420
cttccttgga gcctacgcct acccgccgcg accccaggcg gccggcttcc ccggcgcggg    480
cgagtccttc ccgccgcccg cggacgccga gggctaccag ccgggcgagg gctacgccgc    540
```

```
cccggacccg cgcgccgggc tctacccggg gccgcgtgag gactacgcgc tacccgcggg      600
actggaggtg tcggggaaac tgagggtcgc gctcaacaac cacctgttgt ggtccaagtt      660
taatcagcac cagacagaga tgatcatcac caagcaggga cggcggatgt tcccattcct      720
gtcatttact gtggccgggc tggagcccac cagccactac aggatgtttg tggacgtggt      780
cttggtggac cagcaccact ggcggtacca gagcggcaag tgggtgcagt gtggaaaggc      840
cgagggcagc atgccaggaa accgcctgta cgtccacccg gactccccca acacaggagc      900
gcactggatg cgccaggaag tttcatttgg gaaactaaag ctcacaaaca caagggggc       960 gtccaacaat gtgacccaga tgattgtgct ccagtccctc cataagtacc agccccggct     1020
gcatatcgtt gaggtgaacg acggagagcc agaggcagcc tgcaacgctt ccaacacgca     1080
tatctttact ttccaagaaa cccagttcat tgccgtgact gcctaccaga atgccgagat     1140
tactcagctg aaaattgata taaccccctt tgccaaagga ttccgggaga ctttgagtc      1200 catgtacaca tctgttgaca ccagcatccc ctccccgcct ggacccaact gtcaattcct     1260
tgggggagat cactactctc ctctcctacc caaccagtat cctgttccca gccgcttcta     1320
ccccgacctt cctggccagg cgaaggatgt ggttccccag gcttactggc tgggggcccc     1380
ccgggaccac agctatgggg ctgagtttcg agcagtcagc atgaagcctg cattcttgcc     1440
ctctgcccct gggcccacca tgtcctacta ccgaggccag gaggtcctgg cacctggagc     1500
tggctggcct gtggcacccc agtaccctcc caagatgggc ccggccagct ggttcagccc     1560
tatgcggact ctgcccatgg aacccggccc tggaggctca gagggacggg gaccagagga     1620
ccagggtccc cccttggtgt ggactgagat tgcccccatc cggccggaat ccagtgattc     1680
aggactgggc gaaggagact ctaagaggag gcgcgtgtcc ccctatcctt ccagtggtga     1740
cagctcctcc cctgctgggg cccttctcc ttttgataag gaagctgaag acagtttta      1800 taactattt cccaactgag cagatgacat gatgaaagga acagaaacag tgttattagg      1860
ttggaggaca ccgactaatt tgggaaacgg atgaaggact gagaaggccc ccgctccctc     1920
tggcccttct ctgtttagta gttggttggg gaagtggggc tcaagaagga tttgggtt      1980 caccagatgc ttcctggccc acgatgaaac ctgagagggg tgtccccttg ccccatcctc     2040
tgccctaact acagtcgttt acctggtgct gcgtcttgct tttggtttcc agctggagaa     2100
aagaagacaa gaaagtcttg ggcatgaagg agcttttgc atctagtggg tgggaggggt      2160
caggtgtggg acatgggagc aggagactcc actttcttcc tttgtacagt aactttcaac     2220
cttttcgttg gcatgtgtgt taatccctga tccaaaaaga acaaatacac gtatgttata     2280
accatcagcc cgccagggtc agggaaagga ctcacctgac tttggacagc tggcctgggc     2340 tcccctgct caaacacagt ggggatcaga gaaaagggc tggaaggggg ggaatggccc      2400
acatctcaag aagcaagata ttgtttgtgg tggttgtgtg tgggtgtgtg                2450
```

<210> SEQ ID NO 151
<211> LENGTH: 2399
<212> TYPE: DNA
<213> ORGANISM: Homo sapiens

<400> SEQUENCE: 151

```
ggcgccgtct tgatactttc agaaagaatg cattccctgt aaaaaaaaaa aaaaaatact       60
gagagaggga gagagagaga gaagaagaga gagagacgga gggagagcga gacagagcga      120
gcaacgcaat ctgaccgagc aggtcgtacg ccgccgcctc ctcctcctct ctgctcttcg      180
ctacccaggt gacccgagga gggactccgc ctccgagcgg ctgaggaccc cggtgcagag      240
```

| | | |
|---|---|---|
| gagcctggct cgcagaattg cagagtcgtc gccccttttt acaacctggt cccgttttat | 300 |
| tctgccgtac ccagtttttg gattttttgtc ttccccttct tctctttgct aaacgacccc | 360 |
| tccaagataa ttttttaaaaa accttctcct ttgctcacct ttgcttccca gccttcccat | 420 |
| cccccaccg aaagcaaatc attcaacgac ccccgaccct ccgacggcag gagccccccg | 480 |
| acctcccagg cggaccgccc tccctccccg cgcgcgggtt ccgggccgg cgagagggcg | 540 |
| cgagcacagc cgaggccatg gaggtgacgg cggaccagcc gcgctgggtg agccaccacc | 600 |
| accccgccgt gctcaacggg cagcacccgg acacgcacca cccgggcctc agccactcct | 660 |
| acatggacgc ggcgcagtac ccgctgccgg aggaggtgga tgtgcttttt aacatcgacg | 720 |
| gtcaaggcaa ccacgtcccg ccctactacg aaaactcggt cagggccacg gtgcagaggt | 780 |
| accctccgac ccaccacggg agccaggtgt gccgcccgcc tctgcttcat ggatccctac | 840 |
| cctggctgga cggcggcaaa gccctgggca gccaccacac cgcctccccc tggaatctca | 900 |
| gcccttctc caagacgtcc atccaccacg gctccccggg gccctctcc gtctaccccc | 960 |
| cggcctcgtc ctcctccttg tcgggggggcc acgccagccc gcacctcttc accttcccgc | 1020 |
| ccaccccgcc gaaggacgtc tccccggacc catcgctgtc caccccaggc tcggccggct | 1080 |
| cggcccggca ggacgagaaa gagtgcctca agtaccaggt gcccctgccc gacagcatga | 1140 |
| agctggagtc gtcccactcc cgtggcagca tgaccgccct gggtggagcc tcctcgtcga | 1200 |
| cccaccaccc catcaccacc tacccgccct acgtgcccga gtacagctcc ggactcttcc | 1260 |
| ccccagcag cctgctgggc ggctccccca ccggcttcgg atgcaagtcc aggcccaagg | 1320 |
| cccggtccag cacagaaggc agggagtgtg tgaactgtgg ggcaacctcg accccactgt | 1380 |
| ggcggcgaga tggcacggga cactaccgtg gcaacgcctg cgggctctat cacaaaatga | 1440 |
| acggacagaa ccggccccctc attaagccca agcgaaggct gtctgcagcc aggagagcag | 1500 |
| ggacgtcctg tgcgaactgt cagaccacca caaccacact ctggaggagg aatgccaatg | 1560 |
| gggaccctgt ctgcaatgcc tgtgggctct actacaagct tcacaatatt aacagacccc | 1620 |
| tgactatgaa gaaggaaggc atccagacca gaaaccgaaa aatgtctagc aaatccaaaa | 1680 |
| agtgcaaaaa agtgcatgac tcactggagg acttccccaa gaacagctcg tttaacccgg | 1740 |
| ccgccctctc cagacacatg tcctcccctga gccacatctc gcccttcagc cactccagcc | 1800 |
| acatgctgac cacgcccacg ccgatgcacc cgcatccag cctgtccttt ggaccacacc | 1860 |
| accctccag catggtcacc gccatgggtt agagccctgc tcgatgctca cagggccccc | 1920 |
| agcgagagtc cctgcagtcc ctttcgactt gcattttgc aggagcagta tcatgaagcc | 1980 |
| taaacgcgat ggatatatgt ttttgaaggc agaaagcaaa attatgtttg ccactttgca | 2040 |
| aaggagctca ctgtggtgtc tgtgttccaa ccactgaatc tggacccat ctgtgaataa | 2100 |
| gccattctga ctcatatccc ctatttaaca gggtctctag tgctgtgaaa aaaaaaatgc | 2160 |
| tgaacattgc atataactta tattgtaaga aatactgtac aatgacttta ttgcatctgg | 2220 |
| gtagctgtaa ggcatgaagg atgccaagaa gtttaaggaa tatgggagaa atagtgtgga | 2280 |
| aattaagaag aaactaggtc tgatattcaa atggacaaac tgccagtttt gtttcctttc | 2340 |
| actggccaca gttgtttgat gcattaaaag aaaataaaaa aagaaaaaa gagaaaaga | 2399 |

<210> SEQ ID NO 152
<211> LENGTH: 2365
<212> TYPE: DNA
<213> ORGANISM: Homo sapiens

<400> SEQUENCE: 152

```
tcccagcctt cccatccccc caccgaaagc aaatcattca acgaccccg accctccgac       60 ggcaggagcc ccccgacctc ccaggcggac cgcccttccc tccccgcgcg ggttccgggc      120
ccggcgagag ggcgcgacga cagccgaggc catggaggtg acggcggacc agccgcgctg      180
ggtgagccac caccaccccg ccgtgctcaa cgggcagcac ccggacacgc accacccggg      240
cctcagccac tcctacatgg acgcggcgca gtacccgctg ccggaggagg tggatgtgct      300
ttttaacatc gacggtcaag gcaaccacgt cccgccctac tacggaaact cggtcagggc      360
cacggtgcag aggtaccctc cgacccacca cgggagccag gtgtgccgcc cgcctctgct      420
tcatggatcc ctaccctggc tggacggcgg caaagccctg ggcagccacc acaccgcctc      480
cccctggaat ctcagcccct tctccaagac gtccatccac cacggctccc cggggcccct      540
ctccgtctac cccccggcct cgtcctcctc cttgtcgggg ggccacgcca gcccgcacct      600
cttcaccttc ccgcccaccc cgccgaagga cgtctccccg acccatcgc tgtccacccc      660 aggctcggcc ggctcggccc ggcaggacga gaaagagtgc ctcaagtacc aggtgccccct     720 gcccgacagc atgaagctgg agtcgtccca ctcccgtggc agcatgaccg ccctgggtgg      780
agcctcctcg tcgacccacc accccatcac cacctacccg ccctacgtgc ccagtacag       840 ctccggactc ttccccccca gcagcctgct gggcggctcc cccaccggct cggatgcaa       900 gtccaggccc aaggcccggt ccagcacagg cagggagtgt gtgaactgtg ggcaacctc       960 gaccccactg tggcggcgag atggcacggg acactacctg tgcaacgcct gcgggctcta    1020
tcacaaaatg aacggacaga accggcccct cattaagccc aagcgaaggc tgtctgcagc    1080
caggagagca gggacgtcct gtgcgaactg tcagaccacc acaaccacac tctggaggag    1140
gaatgccaat ggggaccctg tctgcaatgc ctgtgggctc tactacaagc ttcacaatat    1200
taacagaccc ctgactatga agaaggaagg catccagacc agaaaccgaa aaatgtctag    1260
caaatccaaa aagtgcaaaa aagtgcatga ctcactggag gacttcccca agaacagctc    1320
gtttaacccg gccgccctct ccagacacat gtcctccctg agccacatct cgcccttcag    1380
ccactccagc cacatgctga ccacgcccac gccgatgcac ccgccatcca gcctgtcctt    1440
tggaccacac caccccctcca gcatggtcac cgccatgggt tagagccctg ctcgatgctc    1500
acagggcccc cagcgagagt ccctgcagtc cctttcgact tgcattttg caggagcagt     1560 atcatgaagc ctaaacgcga tggatatatg tttttgaagg cagaaagcaa aattatgttt    1620
gccactttgc aaaggagctc actgtggtgt ctgtgttcca accactgaat ctggacccca    1680
tctgtgaata agccattctg actcatatcc cctatttaac agggtctcta gtgctgtgaa    1740
aaaaaaaaat cctgaacatt gcatataact tatattgtaa gaaatactgt acaatgactt    1800
tattgcatct gggtagctgt aaggcatgaa ggatgccaag aagtttaagg aatatgggag    1860
aaatagtgtg gaaattaaga agaaactagg tctgatattc aaatggacaa actgccagtt    1920
ttgtttcctt tcactggcca cagttgtttg atgcattaaa agaaataaa aaaagaaaa      1980 aagagaaaag aaaaaaaaag aaaaaagttg taggcgaatc atttgttcaa agctgttggc    2040
cctctgcaaa ggaaatacca gttctgggca atcagtgtta ccgttcacca gttgccattg    2100
agggtttcag agagcctttt tctaggccta catgctttgt gaacaagtcc ctgtaattgt    2160
tgtttgtatg tataattcaa agcaccaaaa taagaaaaga tgtagattta tttcatcata    2220
ttatacagac cgaactgttg tataaattta tttactgcta gtcttaagaa ctgctttctt    2280
tcgtttgttt gtttcaatat tttccttctc tctcaatttt cggttgaata aactagatta    2340
cattcagttg gcaaaaaaaa aaaaa                                          2365
```

<210> SEQ ID NO 153
<211> LENGTH: 2728
<212> TYPE: DNA
<213> ORGANISM: Homo sapiens
<220> FEATURE:
<221> NAME/KEY: mutation
<222> LOCATION: (57)..(57)
<220> FEATURE:
<221> NAME/KEY: mutation
<222> LOCATION: (59)..(59)
<220> FEATURE:
<221> NAME/KEY: mutation
<222> LOCATION: (69)..(69)
<220> FEATURE:
<221> NAME/KEY: hgd40 bindingsite
<222> LOCATION: (909)..(927)

<400> SEQUENCE: 153

```
ggcgccgtct tgatactttc agaaagaatg cattccctgt aaaaaaaaaa aaaaaaaat      60
actgagagag ggagagagag agaagaagag agagagacgg agggagagcg agacagagcg    120
agcaacgcaa tctgaccgag caggtcgtac gccgccgcct cctcctcctc tctgctcttc    180
gctacccagg tgacccgagg agggactccg cctccgagcg gctgaggacc ccggtgcaga    240
ggagcctggc tcgcagaatt gcagagtcgt cgccccttttt tacaacctgg tcccgttttta   300
ttctgccata cccagttttt ggattttttgt cttcccctctc ttctctttgc taaacgaccc   360
ctccaagata atttttaaaa aaccttctcc tttgctcacc tttgcttccc agccttccca    420
tcccccacc gaaagcaaat cattcaacga ccccgaccc tccgacggca ggagcccccc     480
gacctcccag gcggaccgcc ctccctcccc gcgcgcgggt tccgggcccg gcgagagggc    540
gcgagcacag ccgaggccat ggaggtgacg gcggaccagc cgcgctgggt gagccaccac    600
cacccccgccg tgctcaacgg gcagcacccg gacacgcacc accgggcct cagccactcc   660
tacatggacg cggcgcagta cccgctgccg gaggaggtgg atgtgctttt taacatcgac   720
ggtcaaggca accacgtccc gccctactac ggaaaactcgg tcagggccac ggtgcagagg   780
taccctccga cccaccacgg gagccaggtg tgccgcccgc ctctgcttca tggatcccctc   840
cctggctgga cggcggcaaa gccctgggca gccaccacac cgcctccccc tggaatctca   900
gccccttctc caagacgtcc atccaccacg gctccccggg gcccctctcc gtctaccccc   960
cggcctcgtc ctcctccttg tcgggggggcc acgccagccc gcacctcttc accttcccgc  1020
ccaccccgcc gaaggacgtc tccccggacc catcgctgtc caccccaggc tcggccggct  1080
cggcccggca ggacgagaaa gagtgcctca gtaccaggt gccctgccc gacagcatga    1140
agctggagtc gtcccactcc cgtggcagca tgaccgccct gggtggagcc tcctcgtcga   1200
cccaccaccc catcaccacc tacccgcccct acgtgcccga gtacagctcc ggactcttcc  1260
cccccagcag cctgctgggc ggctccccca ccggcttcgg atgcaagtcc aggcccaagg   1320
cccggtccag cacagaaggc agggagtgtg tgaactgtgg gcaacctcg accccactgt    1380
ggcggcgaga tggcacggga cactacctgt gcaacgcctg cgggctctat acaaaaatga   1440
acggacagaa ccggccccctc attaagccca agcgaaggct gtctgcagcc aggagagcag   1500
ggacgtcctg tgcgaactgt cagaccacca caaccacact ctggaggagg aatgccaatg   1560
ggaccctgt ctgcaatgcc tgtgggctct actacaagct tcacaatatt aacagacccc    1620
tgactatgaa gaaggaaggc atccagacca gaaaccgaaa aatgtctagc aaatccaaaa    1680
agtgcaaaaa agtgcatgac tcactggagg acttccccaa gaacagctcg tttaacccgg   1740
ccgccctctc cagacacatg tcctcccctga gccacatctc gccccttcagc caccccagcc  1800
```

```
acatgctgac cacgcccacg ccgatgcacc cgccatccag cctgtcctttt ggaccacacc    1860 accccctccag catggtcacc gccatgggtt agagccctgc tgatgctcac agggccccca    1920
gcgagagtcc ctgcagtccc tttcgacttg cattttttgca ggagcagtat catgaagcct    1980
aaacgcgatg gatatatgtt tttgaaggca gaaagcaaaa ttatgcttgc cactttgcaa    2040
aggagctcac tgtggtgtct gtgttccaac cactgaatct ggaccccatc tgtgaataag    2100
ccattctgac tcatatcccc tatttaacag ggtctctagt gctgtgaaaa aaaaaaatgc    2160
tgaacattgc atataactta tattgtaaga aatactgtac aatgactttta ttgcatctgg    2220 gtagctgtaa ggcatgaagg atgccaagaa gtttaaggaa tatgggagaa atagtgtgga    2280
aattaagaag aaactaggtc tgatattcaa atggacaaac tgccagtttt gtttcctttc    2340
actggccaca gttgtttgat gcattaaaag aaaataaaaa aaagaaaaag agaaaagaaa    2400
aaaaaagaaa aagttgtag gcgaatcatt tgttcaaagc tgttggcctc tgcaaaggaa    2460
ataccagttc gggcaatcag tgttaccgtt caccagttgc cattgagggt ttcagagagc    2520 cttttttctag gcctacatgc tttgtgaaca agtccctgta attgttgttt gtatgtataa    2580
ttcaaagcac caaaataaga aaagatgtag atttatttca tcatattata cagaccgaac    2640
tgttgtataa attttattttac tgctagtctt aagaactgct ttctttcgtt tgtttgtttc    2700 aatatttttcc ttctctctca attttcgg                                        2728
```

<210> SEQ ID NO 154
<211> LENGTH: 15
<212> TYPE: DNA
<213> ORGANISM: artificial sequence
<220> FEATURE:
<221> NAME/KEY: misc_feature
<222> LOCATION: (1)..(15)
<223> OTHER INFORMATION: Catalytic Domain of DNAzyme against GATA-3mRNA

<400> SEQUENCE: 154

```
ggctagctac aacga                                                         15
```

METHOD FOR PRODUCING A CELL AND/OR TISSUE AND/OR DISEASE PHASE SPECIFIC MEDICAMENT

CROSS REFERENCE TO RELATED APPLICATIONS

This application is a division of U.S. patent application Ser. No. 10/574,560 filed 1 Feb. 2007, which is the US national Phase of PCT/DE 2004/002197 filed 1 Oct. 2004 and claiming the benefit of the priority of German Patent Application 103 46 487.5 filed 2 Oct. 2003.

FIELD OF THE INVENTION

The present invention relates to a method for producing of a cell and/or tissue and/or disease phase specific medicament suitable for the treatment of chronic inflammatory diseases.

BACKGROUND OF THE INVENTION

Chronic inflammatory diseases constitute an increasing medical problem area with a high socio-economic impact. These include in particular the following disease groups:
Autoimmune diseases and rheumatic diseases (manifestations on skin, lungs, kidney, vascular system, connective tissue, musculoskeletal system, endocrine system, among other)
Immediate-type allergic reactions and asthma
Chronic obstructive pulmonary diseases (COPD)
Arteriosclerosis
Psoriasis and contact eczema
Chronic rejection reactions after organ or bone marrow transplant In the last decades, many of these diseases are showing a rising prevalence, not only in the industrial nations, but partly, worldwide. Thus, in Europe, North America, Japan and Australia, more than 20% of the population already suffers from allergic diseases and asthma. Chronic obstructive pulmonary diseases are currently the fifth most common cause of death worldwide and, according to calculations by WHO, will become the third most common cause of death by the year 2020. Arteriosclerosis, with the secondary diseases myocardial infarction, stroke and peripheral arterial occlusion disease, occupy a leading position in the global morbidity and mortality statistics. Psoriasis and contact eczema are, together with neurodermatitis, the most common chronic inflammatory skin diseases.

The so far only insufficiently understood interactions between environmental factors and genetic disposition result in a subsequent defective regulation of the immune system. Here, the following common principles can be established for these different diseases:
(A) An excessive immune response against antigens, which would normally be harmless for humans, is found. These antigens can be environmental matter (e.g. allergens such as pollen, animal hairs, food, mites, chemical substances such as preservatives, dyes, cleaning products). In these cases, the patients develop an allergic reaction. In the case of, for example, active and passive cigarette smoking, chronic obstructive pulmonary diseases (COPD) occur. On the other hand, the immune system can, however, also react against the components of the own organism, recognize them as foreign and start an inflammatory reaction against them. An autoimmune disease develops in these cases. In all cases, harmless, non-toxic antigens are recognized as foreign or dangerous and an inappropriate inflammatory reaction is started.

(B) The diseases proceed in phases which include initiation, progression, i.e. progressing of the inflammatory reaction, and the associated destruction and alteration with loss in organ functionality (so-called remodeling).
(C) The diseases present patient specific subphenotypic characteristic features.
(D) Components of the innate and acquired immunity are later involved in the initiation, maintenance and in the destruction and alteration processes. Under the influence of the innate immunity (important components: antigen presenting cells with their diverse populations and the complement system), the cells of the adaptive immune system (important components: T- and B-lymphocytes) are activated and differentiated. T-cells take over central functions in the following process by differentiating into highly specialized effectors. In doing so, they activate and acquire certain effector mechanisms, including, in particular, the following functions: Production of antibodies, control of the functionality of effector cells of the immune system (such as, for example, neutrophil, basophil, eosinophil granulocytes), feeding back on functions of the innate immune system, influencing the functionality of non-hematopoietic cells, e.g. epithelium, endothelium, connective tissue, bone and cartilage, and, in particular, neuronal cells. This amounts to a special interaction between immune and nervous system, which has led to the development of the concept of neuro-immunological interaction in chronic inflammations.

Due to the complexity and variety of the disease patterns associated with chronic inflammations, an optimal medicament for the treatment of the diseases must meet the following requirements:
(1) Diseases manifest themselves in patient specific (sub) phenotypes. Medicaments must therefore possess a high patient or case specificity.
(2) Diseases proceed in stages and phases. Medicaments must therefore possess a high stage or phase specificity.
(3) The diseases are regulated by cells of different specialization. Medicaments must therefore cause a cell specific intervention.
(4) The diseases manifest themselves in different organs and compartments. Medicaments must therefore possess a high compartment or organ specificity.
(5) Medicaments must be suitable for a long-term therapy. Immune system reactions against the medicaments must therefore be prevented.
(6) The side effect profile of the medicaments must present an acceptable medical and ethical balance between severity index, prognosis and progress of the disease.

None of the currently available established therapies against chronic inflammations meets these criteria in an optimal way. The treatment with immunoglobulin A is known from DE 695 11 245 T2, and the inhibition of phospholipase A2 (PLA2) and/or coenzyme A-independent transacylase (CoA-IT) is known from DE 695 18 667 T2. For this disease, the currently established therapy concepts are centered on unspecific anti-inflammatory therapy, as well as immune suppression. Many of the applied unspecific anti-inflammatory substances, such as ibuprofen, acetylsalicylic acid and paracetamol, are either not effective enough or are afflicted with a high rate of unwanted side effects. Steroids may have, in contrast, a higher potency, but are themselves afflicted with serious side effects, such as hypertonia, diabetes and osteoporosis. New generation immune suppressing medicaments, such as, for example, cyclosporine and tacrolimus, present hepato- and nephrotoxicity.

This situation has led to the search for and the clinical testing of a plurality of new molecules intended to act more specifically on immunological and cell biological defective regulation. These include cytokines, cytokine receptors and anti-cytokines. Problems related to these new therapeutic applications include a lack of cell and organ specificity, development of unwanted immune reactions against these molecules, and poor effectiveness for different phenotypes.

In recent years, attempts are being made to use a new class of catalytic molecules, the so-called "DNAzymes" (Santoro 1997), as therapeutic agents for inactivating genes, the expression of which is the cause of diseases. DNAzymes are single stranded molecules which can, in principle, bind to complementary areas of the RNA and inactivate it through cleavage. The specific use of DNAzymes as therapeutic agents requires, however, that the genes causing the disease, as well as their RNA, are known in detail. This is so far only the case for few diseases.

The DNAzyme described in WO 01/11023A1 binds RelA (p65) mRNA and is thus directed against the transcription factor NF-kB; WO 00/42173 discloses an EGR-1 mRNA binding DNAzyme. WO99/50452 discloses a 10-23 DNAzyme that can be used in a diagnostic method for detecting nucleic acid mutations. None of the currently known antisense molecules and DNAzymes can be used for producing a medicament for the treatment of chronic inflammations in patients.

OBJECTS OF THE INVENTION

The object of the present invention is the provision of cell and/or tissue and/or disease phase specific medicaments which lead to the functional inactivation of ribonucleic acid molecules of transcription factors and factors of signal transduction pathways, the expression of which is involved in the development of chronic inflammatory reactions and autoimmune diseases, and which are suitable for the treatment of chronic inflammatory reactions and autoimmune diseases, thus eliminating the abovementioned disadvantages of the state of the art.

It is a further object of the invention to provide a method for producing cell and/or tissue and/or disease phase specific medicaments, which identifies ribonucleic acid molecules of transcription factors and factors of signal transduction pathways, the expression of which is involved in the development of chronic inflammatory reactions and autoimmune diseases, and functionally inactivates them in target cells.

SUMMARY OF THE INVENTION

According to the present invention these objects are achieved by the specific DNAzymes and by medicaments containing the specific DNAzymes according to the present invention.

The advantage of the invention lies in a functional inactivation of ribonucleic acid molecules of transcription factors and factors of signal transduction pathways for differentiation and/or expression of cytokines which are involved in the development of chronic inflammatory reactions and autoimmune diseases, by means of specific DNAzymes and/or siRNA. This strategy distinguishes itself from conventional but also gene therapeutic approaches by a very high cell and/or tissue and/or disease phase specificity and selectivity, high stability of the molecules and negligible antigenicity. Optimal preconditions for a tailored long-term therapy for patients with chronic inflammatory diseases are created.

Further details and advantages of the present invention will become apparent from the following figure and description.

BRIEF DESCRIPTION OF THE DRAWINGS

FIG. 3: Pool of specific ribonucleic acid molecules according to step b) particularly the DNAzymes td 1 to td 70 against T-bet and their nucleotide sequences (A=Adenine, G=Guanine, C=Cytosine, T=Thymine).

FIG. 4: Nucleotide sequences of human T-bet genes in alignment.
Sequence 1: Human T-bet from database no.: NM 013351.
Sequence 2: Human T-bet (sequenced from pBluescript-SK).
Divergent bases are highlighted in grey, primer locations for T-bet cloning are underlined. The primer locations for the relative quantification on the LightCycler are circled. The localization of the DNAzymes td54 and td69 is highlighted in grey and underlined at the same time, td70 is additionally highlighted in bold letters.
(A=Adenine, G=Guanine, C=Cytosine, T=Thymine)

FIG. 4A: Nucleotide sequence 1 of human T-bet gene from FIG. 4, the individual nucleotide pairs GT and AT drawn therein, highlighted in grey, between which there are further DNAzyme cleavage sites.

Here, the quantity of T-bet mRNA from the control test with nonsense DNAzyme is set equal to 100%.

Figure 1:
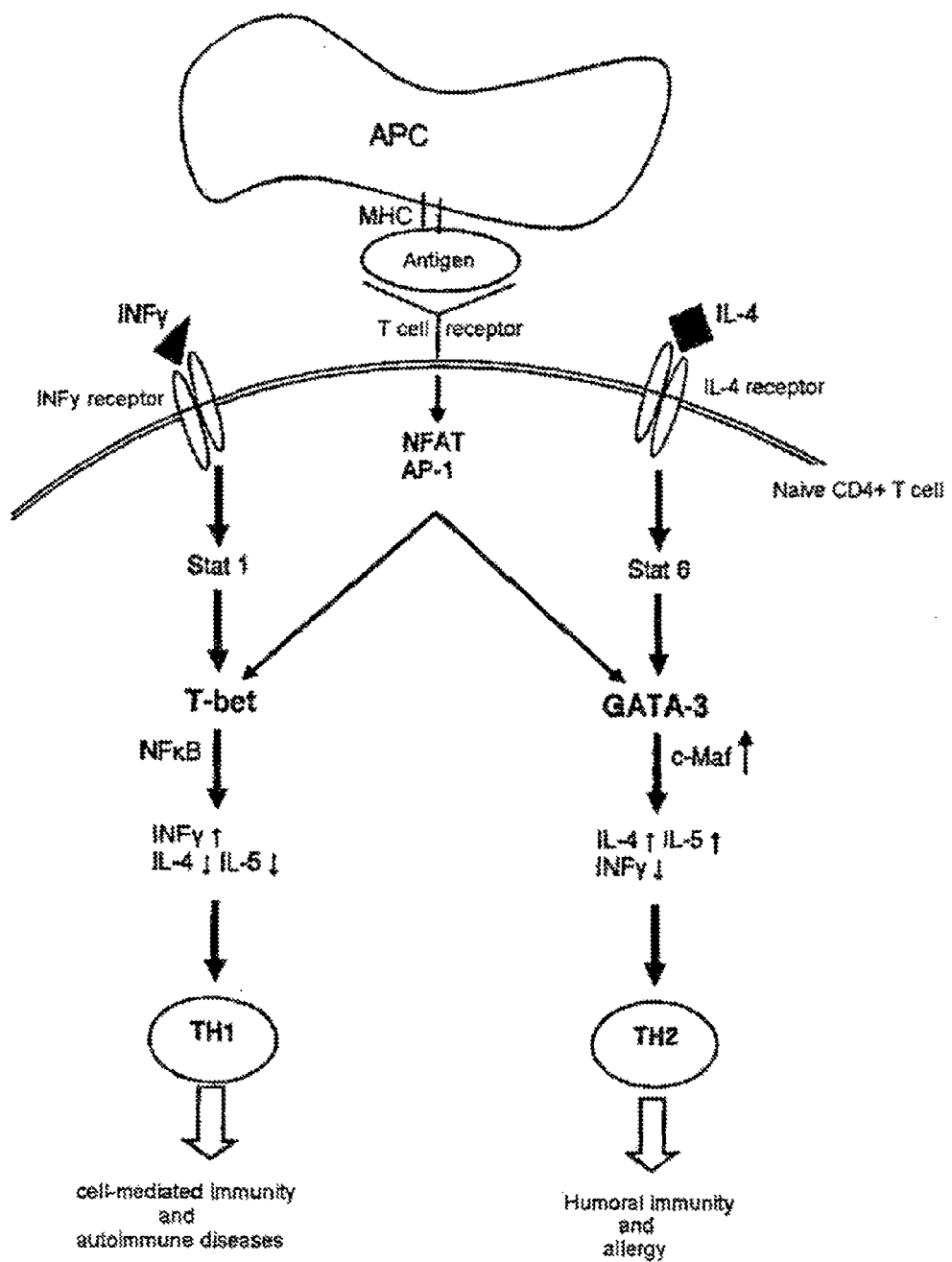
FIG. 1: Schematic representation of the signal transduction during differentiation of CD4+ cells to TH1 and TH2 cells, respectively (modified according to Ho I. C. and Glimcher L. H., Cell 2002; 109; S109-S120).

FIG. 1 shows a schematic representation, modified according to Ho I. C. and Glimcher L. H., Cell 2002; 109; S109-S120, of the dynamics of the signal transduction during differentiation of CD4+ cells to TH1 and TH2 cells, respectively. Stimulation via the T cell receptor through the respective peptide-MHC complex induces the clonal expansion and programmed differentiation of CD4+ T lymphocytes to T helper (TH)1 or TH2 cells. Discrimination between these two subtypes takes place on the basis of their cytokine profiles. TH1 cells produce interferon-y (INFy), interleukin 2 (IL-2) and tumour necrosis factor-B, whereas TH2 cells secrete IL-4, IL-5, IL-9 and IL-13. Bacterial and viral infections induce an immune response that is dominated by TH1 cells. On the other hand, TH2 cells regulate the production of IgE against parasites. TH1 and TH2 cells are in equilibrium with each other. The destruction of this equilibrium causes diseases, an excessive TH1 cell response being associated with autoimmune diseases, while an increased TH2 cell response is the origin of allergic diseases.

It is known that TH1 cytokines are involved in the pathogenesis of autoimmune diseases such as, for example, autoimmune uveitis, experimental allergic encephalomyelitis, type 1 diabetes mellitus or Crohn's disease, while TH2 cytokines (IL-4, IL-5, IL-13 or IL-9) take part in the development of chronic inflammatory airway diseases such as, for example, airway eosinophilia, mucus hypersecretion and airway hyperreactivity. The basis for these diseases are pathophysiological changes during the production of characteristic cytokines by antigen specific TH cells. For instance, transgenic mice which constitutively overexpress the TH2 cytokines IL-4, IL-5, IL-13 or IL-9 in the airway epithelia, show typical allergic inflammatory reactions. In the animal model, TH2 cell subpopulations in the lung and airways induce in TH2 cells the characteristic symptoms of bronchial asthma.

Surprisingly, it was found that transcription factors and factors of signal transduction pathways for differentiation and/or expression of cytokines which are involved in the development of chronic inflammatory reactions and autoimmune diseases, such as, for example, the TH1 cell specific transcription factor T-bet and the TH2 cell specific transcription factor GATA-3, are ideally suited for the cell and/or tissue specific treatment of chronic inflammations or autoimmune diseases.

The TH1 cell specific transcription factor T-bet is, above all, responsible for the differentiation of naive CD+ T cells to TH1 cells. Its expression is controlled by signal transduction pathways of the T cell receptor (TCR) and through INFy receptor/STAT1 T-bet transactivates the endogenous INFy gene and induces the production of INFy. Furthermore, it induces the up-regulation of the protein expression of IL-12Rβ2 chains and leads to chromatin remodeling of individual INFy alleles. The in vivo function of T-bet has been confirmed on knock-out mice (T-bet+). Although T-bet deficient mice present a normal lymphocyte development, CD4+ T cells from these mice produce no INFy, neither when stimulated with anti-CD3/CD28 nor with PMA/ionomycine. T-bet deficient mice display no immune response to a L. major infection, the amount of TH2 cytokines increases.

The function of T-bet in mucosal T cells during the development of inflammatory bowel diseases is known. Investigations on the animal model show a worsening of colitis in reconstituted SCID (Severe Combined Immunodeficiency) mice after retroviral transduction of T-bet in CD4+CD26L+ T cells, while, conversely, the transfer of T-bet deficient T cells does not lead to an induction of colitis.

The transcription factor T-bet specifically induces the development of TH1 cells and controls the production of INFy in these cells. The inhibition of T-bet shifts the balance between TH1 and TH2 cells towards the TH2 cells.

Further transcription factors that play a role in the differentiation to TH1 cells or TH2 cells, respectively, and are involved in the development of chronic inflammatory and autoimmune diseases present an expression which is different in a target cell than compared to a control cell expression and are, according to the present invention, also used in the design of specific DNAzymes and/or siRNA for therapeutic application in chronic inflammatory diseases.

STAT4, STAT5a and STAT1 (signal transducer and activator of transcription)
c-Rel
CREB2 (cAMP response element-binding protein 2)
ATF-2, ATF-2
Hlx
IRF-1 (interferon regulatory factor-1)
c-Maf
NFAT (Nuclear factor of activated T cells)
NIP45 (NF-AT interacting Protein 45)
AP1 (Activator Protein 1)
Mel-18
SKAT-2 (SCAN box, KRAB domain associated with a Th2 phenotype)
CTLA-4 (Cytolytic T lymphocyte-associated antigen 4)

Further factors of the signal transduction pathways that play a role in the differentiation and/or expression of cytokines and are involved in the development of chronic inflammatory and autoimmune diseases exhibit an expression in the target cell that differentiates itself from a control cell expression and are, according to the present invention, also used in the design of specific DNAzymes and/or siRNA for therapeutic application in chronic inflammatory diseases.

Src kinase
Tec kinase
Rlk (Txk in humans)
Itk
Tec
RIBP (Rlk/ltk-binding protein)
PLCy (Phospholipase Cy1)
MAP kinase (Mitogen-activated protein kinase)
ERK
JNK
P38
MKK (MAP kinase kinase)
MKK1
MKK2
MKK3
MKK4
MKK6
MKK7
Rac2
GADD45 (Growth arrest and DNA damage gene 45)
GADD45β
GADD45y
SOCS (Suppressors of cytokine signalling)
CIS (Cytokine-induced SH2 protein)
SOCS1
SOCS2
SOCS3

JAK (Janus kinase)
JAK1
JAK3
NIP45 (NF-AT interacting Protein 45)

According to the present invention, a cell and/or tissue and/or disease phase specific medicament is provided which is suitable for the treatment of chronic inflammatory diseases.

The medicament acts preferably on the intervention points of the complex cascade of immunological and cell biological defective regulations forming the basis for chronic inflammatory reactions and autoimmune diseases. Particularly preferably, these are intervention points in the regulation of the differentiation of the transcription factors involved, such as, for example, the TH1 cell specific transcription factor T-bet. The therapeutic effect achieved is based on a functional inactivation of ribonucleic acid molecules by means of specific DNAzymes and/or SiRNA. This strategy offers a series of advantages compared to conventional, but also gene therapeutic approaches: highest specificity and selectivity, high stability of the molecules and a negligible antigenicity. Optimal preconditions for a tailored long-term therapy for patients with chronic inflammatory diseases are created.

A method for producing of a cell and/or tissue and/or disease phase specific medicament is provided comprising the steps of:
a) Identification of ribonucleic acid molecules the expression of which is different in a target cell than compared to a control cell expression
b) Design of specific ribonucleic acid molecules which bind to ribonucleic acid molecules from step a) and functionally inactivate them
c) Introduction of specific ribonucleic acid molecules from step b) into target cells
d) Formulation of the specific ribonucleic acid molecules from step b) and/or a target cell from step c) into a medicament In the sense of the present invention, the term "cell and/or tissue and/or disease phase specific" means that the medicament produced by means of the method according to the present invention is substantially only effective in a certain type of cell (target cell) and/or in certain tissues or organs and/or in certain phases of the disease, and has a negligible influence on other cells (control cells) tissues or organs. Preferably the medicament is effective in at least $2/3$ of the target cells, more preferably in at least 80% and most preferably on at least 98% of the target cells. It is further preferred that the medicament is effective in no more than 10% of the control cells, more preferred in no more than 5% and most preferred in <1% of the control cells.

In the present invention the term "Identification of ribonucleic acid molecules the expression of which is different in a target cell than compared to a control cell expression" comprises the following points:
i) Target cells are cells in tissues and organs which are known to lead to the development of a disease, contribute thereto or aggravate that disease, which support the processes sustaining the disease, contribute thereto or compound those processes, or which lead to late effects of a disease, contribute thereto or aggravate those effects. They include, for example, cells which present certain transcription factors, secrete specific hormones, cytokines and growth factors, or cells with typical surface receptors.
ii) The target cells can be isolated, for example, by means of technologies which are based on the binding of specific antibodies. Magnetic Beads, obtainable from the companies Miltenyi (Macs-System), Dynal (DynaBeads) or BD-Bioscience (iMAG) are used here. Alternatively, this takes place through cell purification by means of fluorescent labelled antibodies on cell sorters, for example from the company Cytomation (MOFLO) or BD-Bioscience (FACS-Vantage). The purity of the target cells is preferably at least 80%, more preferably at least 95% and most preferably at least 99%.
iii) Methods for isolating RNA are described, e.g. in Sambrook and Russell, Molecular Cloning, A Laboratory Manual, 3. edition, Cold Spring Harbor Laboratory (2001), New York and Ausubel et al., Current Protocols in Molecular Biology, John Wiley & Sons (1998), New York. In addition, it is possible for the average person skilled in the art, to use commercially available kits for RNA isolation (silica technology) e.g. the RNeasy kit from the company Qiagen. It is further preferable to purify mRNA directly from the target cells by using commercial kits, for example from the companies Qiagen (Oligotex mRNA kit), Promega (PolyATract mRNA Isolation System) or Miltenyi (mRNAdirect).
iv) Identification of incrementally different mRNAs, i.e. mRNAs with an expression in the target cell that is higher than the control cell, is conducted, for example, with commercially obtained gene chips (e.g. MWG, CLON-TECH)] or with a filter hybridization method (e.g. Unigene), according to the manufacturer's instructions. Alternatively, differential mRNAs are produced by subtractive hybridization of cDNA which had previously been created from the mRNA through RT reaction. Included in these methods known to the person skilled in the art are, for example, the SSH method (Clontech) or the RDA method. A further preferred application form includes the combination of chip technology and subtractive hybridization. Identification of the differentially expressed genes is carried out using chip technology with the help of commercially available programs, e.g. with the Vector Xpression program from the company InforMax. When using subtractive hybridization, after isolation of the differentially expressed genes by means of conventional methods known to the person skilled in the art, such as cloning and subsequent sequencing (see e.g. Sambrook and Russell, Molecular Cloning, A Laboratory Manual, 3. edition, Cold Spring Harbor Laboratory (2001), New York and Ausubel et al., Current Protocols in Molecular Biology, John Wiley & Sons (1998), New York), a sequence alignment in a data base such as, for example, GenBank (www.ncbi.nlm.nih.gov) is carried out. The expression within the target cell is different compared to the expression in a control cell. In an embodiment of the method according to the present invention the expression in the target cell is higher than the expression in a control cell, preferably at least by a factor 1.5. In a particularly preferred embodiment the expression in the target cell is higher than the expression in a control cell by at least a factor 5, and in a most preferred embodiment the expression is only detectable in the target cell but not in the control cell.

In the sense of the present invention, the term "Design of ribonucleic acid molecules which bind to ribonucleic acid molecules from step a) and functionally inactivate them" comprises the use of RNA inactivating DNA enzymes (DNAzymes) and/or small interfering RNA (siRNA), which functionally inactivates ribonucleic acid molecules.

According to the present invention the term DNAzymes hereby comprises DNA molecules that specifically identify and cleave the target sequence of the nucleic acid, both DNA and RNA.

The "10-23" model represents a general DNAzyme model. DNAzymes of the 10-23 model—also called "10-23 DNAzymes"—possess a catalytic domain of 15 deoxyribonucleic acids, which is flanked by two substrate binding domains. The length of the substrate binding domains is variable, they can either be of the same or of different length. In a preferred embodiment, the substrate binding domains are between 6 and 14 nucleotides long. In a particularly preferred embodiment the substrate binding domains are fully complementary to the region flanking the cleavage site. To bind to and cleave the target RNA, the DNAzyme must not necessarily have to be fully complementary. In vitro investigations show that DNAzymes of the 10-23 type cleave the target RNA at purine-pyrimidine sequences.

To use DNAzymes in the treatment of diseases, preferably, the DNAzymes are stabilized as well as possible against degradation within the body (in the blood, in the intracellular environment, etc.). In a preferred embodiment, a 3'-3' inversion is introduced at one or more ends of the DNAzyme. The term 3'-3' inversion denotes a covalent phosphate bond between the 3' carbon atoms of the terminal nucleotide and the adjacent nucleotide. This type of bond is located, as opposed to the normal phosphate bond, between the 3' and 5' carbon atoms of consecutive nucleotides. Accordingly, it is preferred that the nucleotide on the 3' end is inverse to the of the 3' end of the substrate binding domain adjoining the catalytic domain. In addition to the inversions, DNAzymes can comprise modified nucleotides or nucleotide compounds. Modified nucleotides contain, e.g. N3'-P5' phosphoramidate compounds, 2'-O-methyl substitutions and peptide nucleic acid compounds. Their production is known to the person skilled in the art.

Although the potential DNAzyme cleavage sites occur ubiquitously, they are often blocked by the secondary RNA structure and are thus inaccessible to the DNAzymes. For this reason, only those DNAzymes with freely accessible cleavage sites are selected from a DNAzyme pool. These selected DNAzymes are active, cleave the target mRNA, thus functionally inactivating it. The efficiency of the mRNA cleavage by the individual DNAzymes is shown either by individual testing of each DNAzyme or by coupled testing of multiple DNAzymes in "multiplex assays" (described, e.g. in Cairns et al., 1999).

According to the present invention, the term siRNA comprises 21-23 base long RNA molecules which lead to a specific degradation of the complementary target mRNAs, both in vitro and in vivo. On the basis of the available literature (e.g. http://www.mpibpc.gwdg.de/abteilungen/100/105/index.html), the person skilled in the art is familiar with the production of siRNA molecules starting from the target mRNA sequence. The probability that among three selected siRNA molecules at least one of them is highly active (inhibition of the target RNA by at least 80%), is stated as being at least 70% in the literature. From a pool of siRNA molecules, only those are selected which lead to a specific degeneration of the complementary target mRNA, both in vitro and in vivo.

In the sense of the present invention, the term "introduction of the specific ribonucleic acid molecules from step b) into target cells" comprises the transfection into the target cells of vectors, particularly plasmids, cosmids, viruses or bacteriophages, which contain the previously described specific ribonucleic acid molecules according to the present invention. Preferably, the vectors are suited for transformation of animal and human cells and allow the integration of the ribonucleic acid molecules according to the present invention. Transfection methods such as, for example, lipofection with DMRIE-C from the company Invitrogen are known to the person skilled in the art from the literature. In principle, liposomal vectors are also suited therefor. The target molecules are transcription factors, cells secreting hormones, cytokines and growth factors, but also cells carrying the expressed receptors on the surface.

The control cells in the sense of the invention are healthy cells from the target tissue, cells of the same type from other compartments of the same patient or also from healthy individuals.

Cultivation of the target cell is carried out in culture media adapted to the requirements of the target cell in regard to pH value, temperature, salt concentration, antibiotics, vitamins, trace elements and ventilation. The term patient relates equally to humans and vertebrates. The medicament can therefore be used in both human and veterinary medicine.

The term "Formulation of the specific ribonucleic acid molecules from step b) or a target cell from step c) into a medicament" comprises pharmaceutically acceptable compositions containing modifications and "prodrugs", as long as they do not trigger excessive toxicity, irritations or allergic reactions in the patient after conducting a reliable medical assessment. The term "prodrug" relates to compounds which are transformed to improve their absorption, for example, by hydrolysis in the blood.

Preferably, the formulation permits the specific ribonucleic acid molecules to be administered to the patient in form of a pharmaceutically acceptable composition, either orally, rectally, parenterally, intravenously, intramuscularly or subcutaneously, intracisternally, intravaginally, intraperitoneally, intrathecally, intravascularly, locally (powder, ointment or drops) or in spray form.

Dosing forms for local administration of the medicament of this invention comprise ointments, powders, sprays or inhalation means. The active component is admixed under sterile conditions, depending on the requirements, with a physiologically acceptable carrier substance and possible preservatives, buffers or propellants.

The dosing method is determined by the treating physician in accordance with the clinical factors. It is known to the person skilled in the art that the dosing method is dependent on different factors, such as, for example, body size, weight, body surface area, age, sex or the general health of the patient, but also on the specific substance to be administered, the duration and type of administration, and on other medicaments which are possibly administered in parallel.

The medicament produced with the method according to the present invention possesses a high patient, disease, stage and phase specificity. It causes a cell specific intervention and is specific for compartments and organs. No or only very limited reactions of the immune system develop against the medicament and the side effect profile is commensurate with severity index, prognosis and progression of the disease.

The medicament can be used in the therapy of all disease groups associated with chronic inflammations, such as, for example, autoimmune diseases, rheumatic diseases (manifestations on skin, lungs, kidney, vascular system, connective tissue, musculoskeletal system, endocrine system, among other), immediate-type allergic reactions and asthma, chronic obstructive pulmonary diseases (COPD), arteriosclerosis, psoriasis and contact eczema, and also in the therapy of chronic rejection reactions after organ or bone marrow transplant.

EXECUTION EXAMPLE a) Identification of Ribonucleic Acid Molecules the Expression of which is Different in a Target Cell than Compared to a Control Cell Expression i) The naive CD4+ cells responsible for the development of chronic inflammatory reactions are used as target cells.

ii) The CD4+ target cells are isolated using magnetic beads (from Miltenyi (Macs System) Dynal (DynaBeads) or BD-Bioscience (iMAG)), alternatively on cell sorters by means of fluorescent labelled antibodies, e.g. from the companies Cytomation (MOFLO) or BD Bioscience (FACSVantage).

iii) RNA isolation is carried out according to standard methods; see Sambrook and Russell, Molecular Cloning, A Laboratory Manual, 3. edition, Cold Spring Harbor Laboratory (2001), New York and Ausubel et al., Current Protocols in Molecular Biology, John Wiley & Sons (1998), New York.

Alternatively, an RNeasy kit from the company Qiagen is used, or the mRNA is isolated directly from CD4+ target cells using the Oligotex mRNA kit from the company Qiagen, according to manufacturer's instructions.

iv) Identification of incrementally different mRNAs, i.e. mRNAs with a higher expression in the target cell than the control cell, is conducted with gene chips (e.g. MWG, CLONTECH), and the identification of the differentially expressed genes is carried out by means of the Vector Xpression program from the company InforMax.

Figure 2:
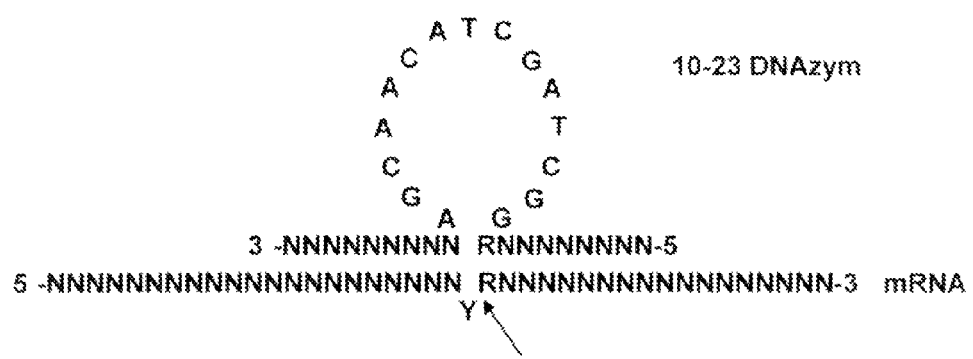
FIG. 2: Nucleotide sequence of the catalytic domain of the 10-23 DNAzyme and binding to a target RNA by means of Watson-Crick pairing. ®=A or G; Y=U or C, N=A, G, U or G). The arrow indicates the cleavage site on the target mRNA.

Filter hybridization method (e.g. Unigene), according to manufacturer's instructions. The isolation of the differentially expressed genes is followed by cloning, sequencing (according to standard procedures, see e.g. Sambrook and Russell, Molecular Cloning, A Laboratory Manual, 3. edition, Cold Spring Harbor Laboratory (2001), and sequence alignment in the gene data base (www.ncbi.nlm.nih.gov). The expression of T-bet is different in the target cell (Th1 cell) in comparison with the expression in a control cell (Th0 cell).

b) Design of Specific Ribonucleic Acid Molecules which Bind to Ribonucleic Acid Molecules from Step a) and Functionally Inactivate them FIG. 3 shows the pool td1-td78 of specific DNAzymes according to the present invention against T-bet mRNA. The DNAzymes have a total length of 33 nucleotides, with the central catalytic domain corresponding to 15 nucleotides (in lowercase letters) of the catalytic domain of the known 10-23 DNAzyme (FIG. 2). This catalytic domain is flanked by two right and left is substrate binding domains (in uppercase letters), each comprising 9 nucleotides. The nucleotide sequence of the right and left substrate binding domain is different and varies for the DNAzymes td1 to td78, so that a different specific bond takes place by means of Watson-Crick pairing to the T-bet mRNA.

FIG. 2 shows the general model for binding the 10-23 DNAzymes to an arbitrary target RNA, labelled N, wherein the arrow points to the cleavage site on the target mRNA. Since it is known from literature that DNAzymes cleave the target mRNA at purine-uracil more effectively than at purine-cytosine bonds, DNAzymes which cleave at purine-uracil bonds are preferably constructed.

The model shown in FIG. 2 can be applied, in terms of its operating principle, to the binding of the DNAzymes td1 to td78 to T-bet mRNA.

The DNAzymes td1 to td78 are used unmodified for in vitro tests and modified for tests on cell cultures (purchased through the company Eurogentec). The following modifications were applied for stabilization and protection:
1) A stabilizing inverse thymidine on the 3' end.
2) a FAM label on the 5' end to assess the transfection efficiency of the cells by means of FACS analysis.

To present the cleavage properties of the DNAzymes and the functional inactivation of the target mRNA of the T-bet mRNA, in vitro transcription of the T-bet mRNA from human EDTA whole blood is carried out by means of a QIAamp RNA Blood Mini Kit (Qiagen, Germany), according to manufacturer's instructions.

Figure 4:
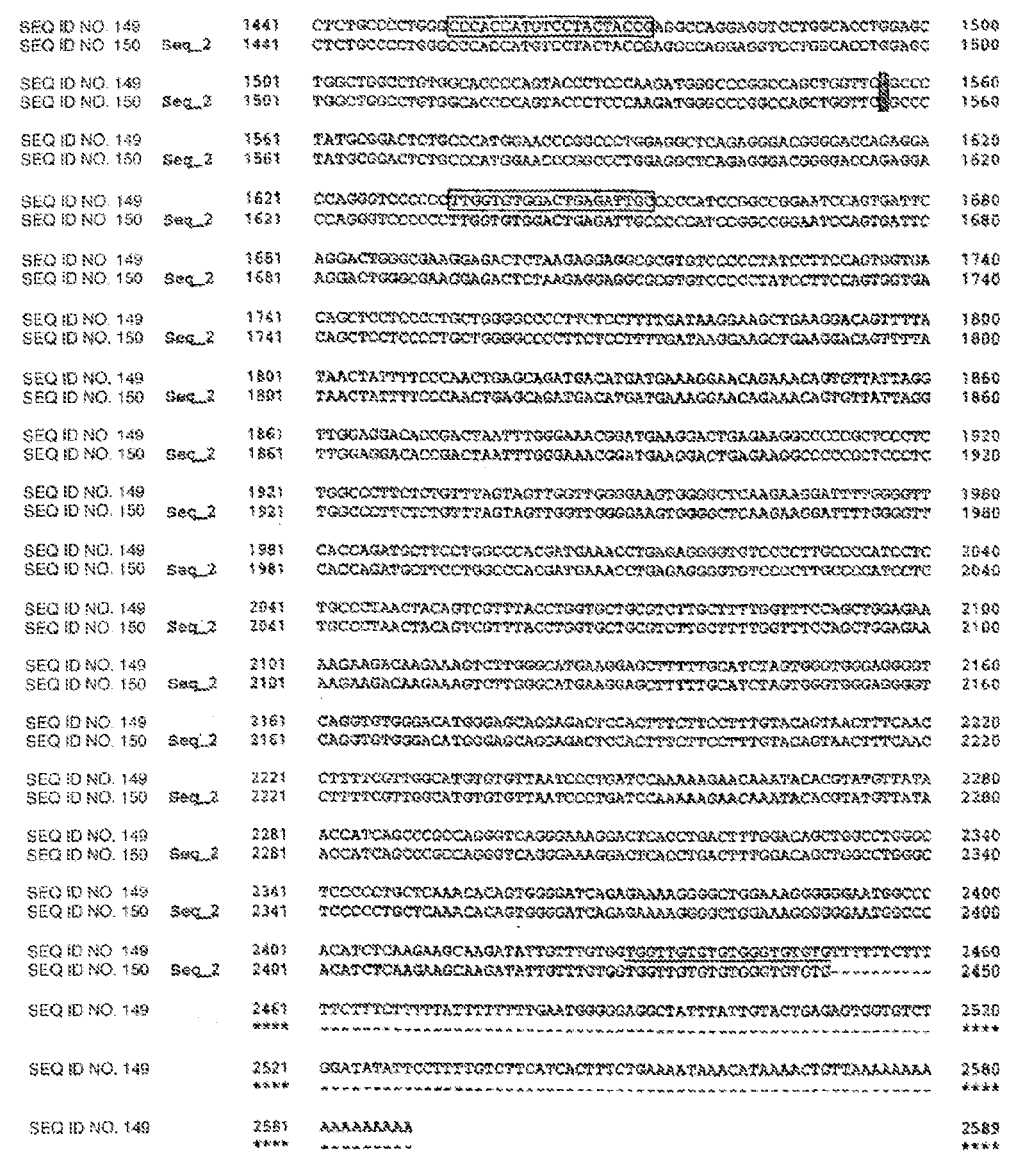

FIG. 4 shows the nucleotide sequence of human T-bet, as obtained from the database entries [PubMed (http://www.ncbi.nlm.nih.gov/entrez/query.fcgi?db=Nucleotide)] no.: NM_013351, sequence 1.

The reverse transcription takes place with the forward primer CGGCCCGCTGGAGAGGAAGC and reverse primer CACACACCCACACACAACC in accordance with standard procedures (ThermoScript from Invitrogen), with amplification of a 2450 nucleotide long PCR product. This PCR product is cloned into the pBluescript-SK (Stratagene) using standard procedures and sequenced for verification.

FIG. 4 shows a comparison between the nucleic acid sequence of T-bet no.: NM_013351 (sequence 1) and the sequenced sequence (sequence 2). It shows that the sequences are not totally identical, with individual bases being interchanged. The nucleic acid sequence 2 of T-bet in FIG. 4 forms, according to the present invention, the basis for the construction of DNAzymes against T-bet mRNA.

FIG. 4A shows the nucleotide sequence of sequence 1 of the human T-bet gene from FIG. 4 and, drawn therein with grey highlight, two nucleotides GT or AT, respectively, between which there are further potential cleavage sites for DNAzymes.

Production of T-bet mRNA is carried out after linearization of the T-bet containing plasmid pBluescript-SK by cleaving with the restriction enzyme Xba I (Fermentas) and through in vitro transcription according to the manufacturer's instructions (Ambion). T-bet mRNA is present with a length of a total of 2550 nucleotides.

The in vitro cleavage experiments of T-bet mRNA with the DNAzymen (td1 to td78) are conducted in a volume of 10 l comprising the following reaction composition: 50 mM Tris pH 7.4, 150 mM NaCl, 10 mM MgCl2, 0.25 M DNAzyme and 0.025 M T-bet mRNA transcribed in vitro (at a substrate to DNAzyme ratio of 1:10). The reactions are incubated at 37° C. for the times indicated for each case. The reaction is stopped by adding formamide and EDTA containing RNA Sample Loading Buffer (Sigma). The denatured samples are separated on 1.3% TAE agarose gels and analyzed in the UV transilluminator.

Figure 5:
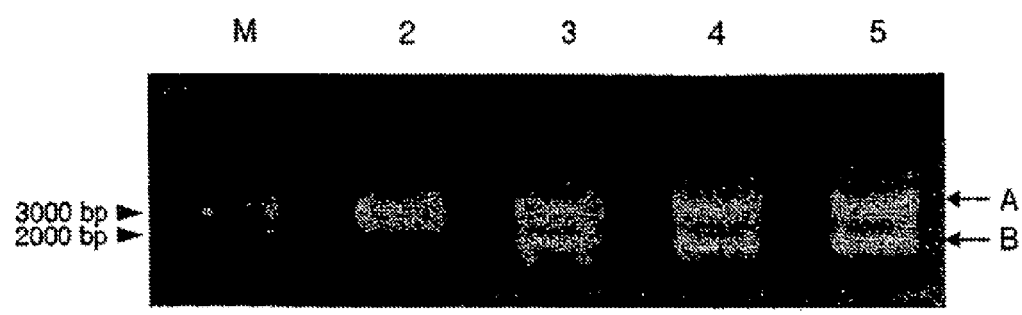
FIG. 5: Gel electrophoresis showing the cleavage of a target mRNA (here T-bet mRNA) with specific ribonucleic acid molecules according to step b), here modified DNAzymes [td54m (lane 3), td69m (lane 4) and td70m (lanes)]. The modified DNAzymes (0.25 M) are incubated for 30 min at 37° C. with in vitro transcribed T-bet mRNA (0.025 M) in a volume of 10 l comprising the following reaction composition: 50 mM Tris pH 7.4, 150 mM NaCl, 10 mM MgCl2. The products are subsequently separated by means of gel electrophoresis. Lane M contains a 3000 base and 2000 base length standard run in parallel, lane 2 contains a control mRNA with no added DNAzyme. Arrow A points at the band with substrate (here T-bet mRNA), arrow B points at the larger cleavage product. The second cleavage product is smaller and no longer visible in this figure.

FIG. 5 shows as the result of the gel electrophoresis the cleavage of the T-bet target mRNA with modified DNAzymes [td54-M (lane 3), td69-M (lane 4), td70-M (lane 5)]. Lane 2 contains a control T-bet mRNA with no added DNAzyme. A length standard run in parallel (lane M) shows band sizes of 2000 bp and 3000 bp. The arrows point at A, the band containing the substrate (here T-bet mRNA) and B, one of the two cleavage products (the other cleavage product is not shown in this figure).

The comparison between all 78 DNAzymes shows that td54, td69 and td70 are particularly active, the modifications not decreasing the effectiveness of the DNAzyme.

The following table shows the classification of the DNAzyme td 1 to td 78 against t-bet-3 mRNA in 4 groups. This classification is conducted on the basis of in vitro activity tests of the DNAzymes against t-bet mRNA. Group 1: high cleavage activity, group 2: average is cleavage activity, group 3: weak cleavage activity, and group 4: no measurable cleavage activity.

| Group | td | Activity against t-bet mRNA |
|---|---|---|
| 1 | 54, 69, 70 | High cleavage activity |
| 2 | 21, 24, 28, 29, 30, 45, 71, 72, 77, 78 | Average cleavage activity |
| 3 | 13, 19, 22, 23, 25, 27, 31, 32, 44, 46, 47, 48, 50, 51, 53, 55, 56, 57, 58, 60, 61, 62, 65, 67, 68, 73, 74, 75 | Weak cleavage activity |
| 4 | 1, 2, 3, 4, 5, 6, 7, 8, 9, 10, 11, 12, 14, 15, 16, 17, 18, 20, 26, 33, 34, 35, 36, 37, 38, 39, 40, 41, 42, 43, 49, 52, 59, 63, 64, 66, 76 | No cleavage activity | c) Introduction of Specific Ribonucleic Acid Molecules from Step b) into Target Cells The DNAzymes td54, td69 and td70 are used in target cells with and without the described modifications.

For this, Jurkat E6.1 cells (human acute T cell leukemia cells) are cultivated in the RPMI medium with 100 U/ml penicillin, 0.1 mg/ml streptomycin and 10% FKS at 37° C. in a humidified 5% CO2 atmosphere. The transfections are carried out in 6-well plates. For this, 2×106 Jurkat E6.1 cells are introduced in an Opti-MEM I cell culture medium (Invitrogen) and transfected by means of DMRIE-C (Invitrogen) with the modified DNAzymes (0.3 M) (according to manufacturer's instructions of the company Invitrogen). After a 10 hour incubation in the incubator under the abovementioned conditions, the RPMI medium (containing the additions indicated above) is added and the incubation continued for a further 14 hours. The cells are washed with Opti-MEM medium and subsequently transfected again following the protocol described above. The transfection efficiency is assessed after each transfection by means of FACS analysis.

After transfection of Jurkat E6.1 cells the quantity of T-bet mRNA relative to GAPDH mRNA expression is determined quantitatively by means of real-time PCR (LightCycler, Roche) to obtain information on the in vitro effectiveness of the DNAzymes.

For LightCycler analyses the RNA from the Jurkat E6.1 cells is purified by means of RNeasy Mini Kit (Qiagen, Germany) and subsequently normalized photometrically. After reverse transcription with SuperScript II (Gibco) in accordance with manufacturer's instructions follows the quantitative analysis of the T-bet mRNA and GAPDH mRNA in the LightCycler. The total volume for the PCR is of 20 l, containing 1 l DNA, 1 l (0.5 M) for each the sense and the antisense primer, as well as 10 l QuantiTect SYBR Green PCR Master Mix (Qiagen, Germany). The PCR primers used for T-bet are: Sense 5'-CCCACCATGTCCTACTACCG-3; Antisense 5'-GCAATCTCAGTCCACACCAA-3'. The PCR primers used for GAPDH are: Sense 5'-CCCACCATGTCCTAC-TACCG-3; Antisense 5'-GCAATCTCAGTCCACACCAA-3'. The PCR conditions are: Denaturation (15 min 95° C.), amplification (15 sec 95° C., 25 sec 59° C., 25 sec 72° C. for 50 cycles) then final extension 2 min 72° C. The following melting curve is generated as follows: 0 sec 95° C., 15 sec 60° C. then increase the temperature to 97° C. in 0.2° C. increments, simultaneously measuring the fluorescence. The melting curve is used for internal control since all PCR products have a specific melting temperature.

SYBR Green is a fluorescent dye (included in the QuantiTect SYBR Green PCR Master Mix) that binds double stranded DNA. When the DNA is doubled during the extension, SYBR Green binds to it generating a bond dependent fluorescence signal which is detected by the LightCycler at the end of every extension. The higher the quantity of initial material, the earlier a significant increase in the fluorescence will be detected. The LightCycler software provides a graphical representation of the collected fluorescence intensities against the cycles.

Figure 6:
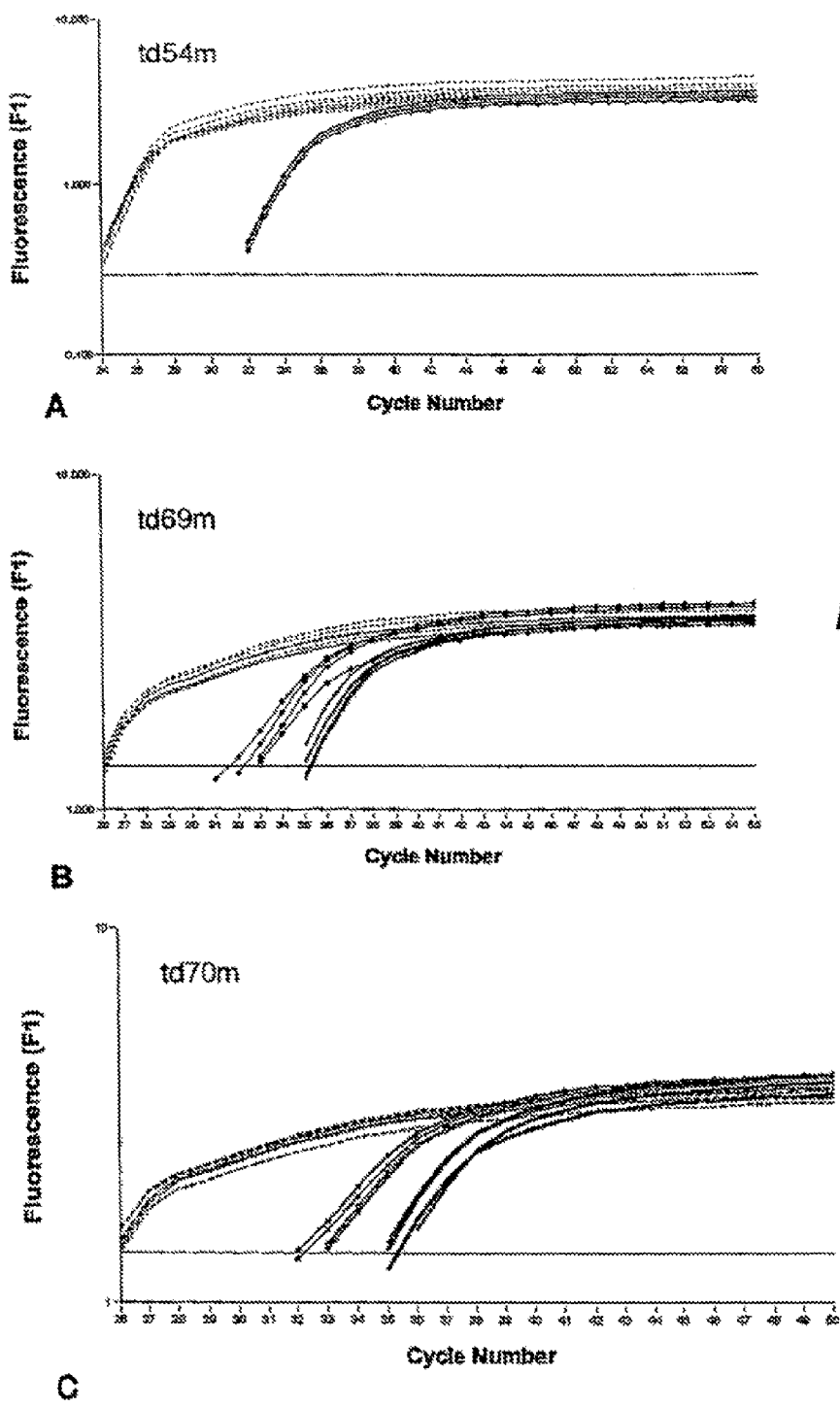
FIG. 6: Quantification on the LightCycler of T-bet and GAPDH mRNA from cells treated with DNAzymes td54 (A), td69 (B) and td70 (C). Jurkat E6.1 cells are transfected twice in a period of 24 h, either with the T-bet specific DNAzymes td54 (A), td69 (B) and td70 (C) or with nonsense DNAzymes for control (not shown). After subsequent cleaning with RNA, a reverse transcription is carried out and the obtained DNA introduced in the LightCycler. GAPDH (dashed lines) is used as internal standard. Shown are 4 measurements each of cells treated with T-bet specific DNAzymes or nonsense DNAzyme. The solid lines show the quantity of T-bet in the cells treated with T-bet specific DNAzymes, dotted lines show the quantity of T-bet in the cells treated with nonsense DNAzyme.
Figure 7:
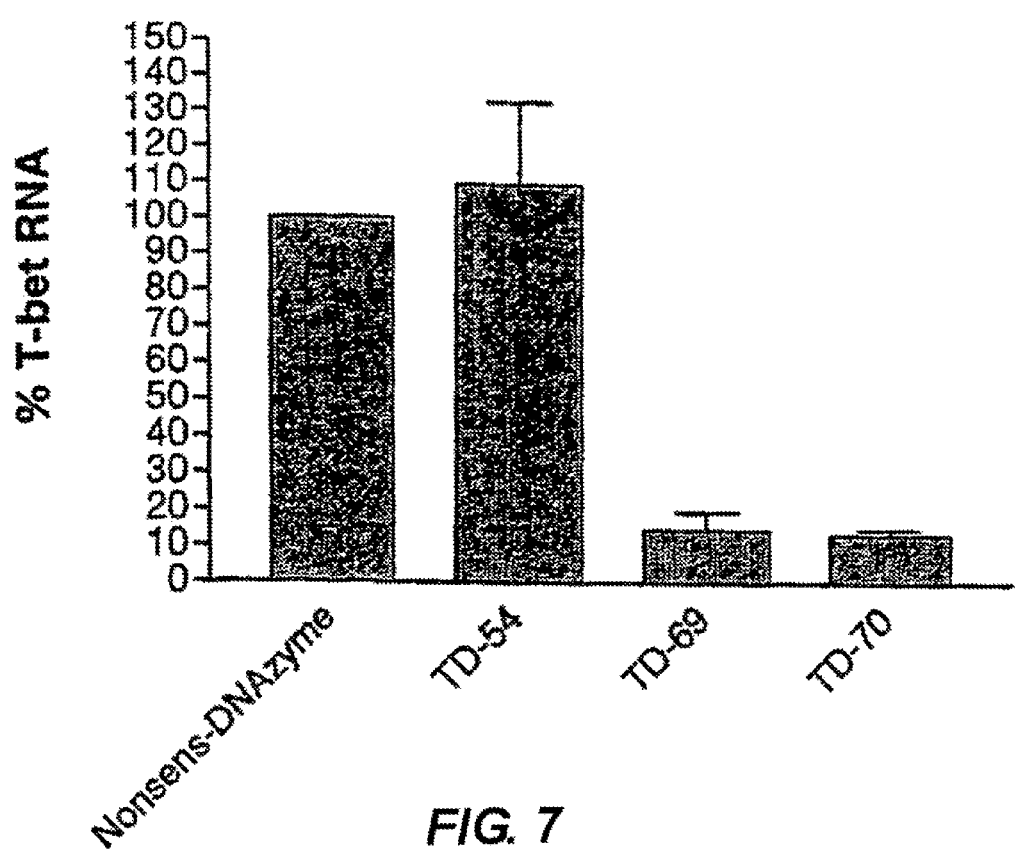
FIG. 7: Diagram of the relative quantification of T-bet mRNA in Jurkat E6.1 cells.
Jurkat E6.1 cells are transfected twice with T-bet specific DNAzymes td54, td69 and td70, and isolated with RNA after 48 h. After a reverse transcription, the quantity of mRNA is determined by means of LightCycler. Nonsense DNAzyme is used as control. The relative quantification of T-bet and GAPDH mRNA is carried out according to instructions [described in the User Bulletin #2 (ABI Prism 7700 Sequence detection System User Bulletin #2 (2001). Relative quantification of gene expression. Http://docs.appliedbiosystems.com/pebiodocs/04303859.pdf)].

FIG. 6 shows LightCycler amplification curves of T-bet mRNA and GAPDH mRNA after treatment of Jurkat E6.1 cells with the DNAzymes td54m, td69m and td70m in comparison to those treated with nonsense-DNAzyme. The individual crossing point (Ct), defined as the PCR cycle at which the fluorescence first distinguishes itself significantly from the background fluorescence, is determined manually with the fit point method of the LightCycler software. The relative quantification of T-bet mRNA and GAPDH mRNA in cells treated with DNAzymes compared with cells treated with nonsense DNAzyme is carried out according to the instructions described in the User Bulletin #2 (ABI Prism 7700 Sequence detection System User Bulletin #2 (2001) Relative quantification of gene expression http://docs.appliedbiosystems.com/pebiodocs/04303859.pdf). Here, the quantity of T-bet mRNA from the control test is set equal to 100%. The data from the relative quantification are represented graphically in FIG. 7.

Compared to nonsense DNAzyme treatment, it is shown that the td69m DNAzyme leads to a suppression of 81.3% and the td70m DNAzyme to a suppression of 81.0%, while the td54m DNAzyme has no suppressive effect on T-bet mRNA.

This means that the td54m DNAzyme is not active in vivo, while td69m and td70m DNAzymes inactivate the mRNA of T-bet also in the cellular environment. The specific in vivo reduction of the T-bet mRNA by the DNAzyme td69m and td70m hence provides an effective therapeutic tool for the treatment of chronic inflammatory diseases.

d) Formulation of the Specific Ribonucleic Acid Molecules from Step b) and/or a Target Cell from Step c) into a Medicament The analysis of different DNAzymes with a substrate domain specific to T-bet shows that DNAzymes td69 and td70 specifically inhibit the T-bet expression in vivo and are suitable as specific ribonucleic acid for the production of a cell and/or tissue and/or disease phase specific medicament.

For this, td69 (GGCAATGAAggctagctacaac-gaTGGGTTTCT) or td70 (TCACGGCAAggctagctacaac-gaGAACTGGGT) or cells transfected with td69m or td70, respectively, are provided in a pharmaceutical composition with a pharmaceutically acceptable carrier for example liposomes or biodegradable polymers.

Alternatively to the DNAzymes, the use of siRNA is proposed for the specific inhibition of the T-bet expression and for the production of a cell and/or tissue and/or disease phase specific medicament. Preferably this is siRNA for inhibiting human T-bet. The production of siRNA is known to the person skilled in the art and described in the literature. The following is an example for siRNA sequences:

| Source | Nucleic acid sequences |
|---|---|
| Human T-bet | Sense strand: UCAGCACCAGACAGAGAUGdTdT<br>Antisense strand: CAUCUCUGUCUGGUGCUGAdTdT |

It is evident to the person skilled in the art that with the teachings of the present invention specific DNAzymes and siRNAs can also be easily produced as medicament for chronic inflammatory diseases and autoimmune diseases, which are directed against further transcription factors that play a role in the differentiation to TH1 or TH2 cells, respectively, for example STAT4, STAT5a, STAT1, c-Rel, CREB2, ATF-2, ATF-2, Hlx, IRF-1, c-Maf, NFAT, NIP45, AP1, Mel-18, SKAT-2, CTLA-4 or which are directed against further factors of the signal transduction pathways for differentiation and/or expression of cytokines, for example Src kinase, Tec kinase, Rlk (Txk in humans), ltk, Tec, RIBP, PLCy, MAP kinase, ERK, JNK, P38, MKK, MKK1, MKK2, MKK3, MKK4, MKK6, MKK7, Rac2, GADD45, GADD45B, GADD45y, SOCS, CIS, SOCS1, SOCS2, SOCS3, JAK, JAK1, JAK3, NIP45.

These Proteins present an expression which is higher in a target cell when compared to the expression in a control cell.

What is claimed is:

1. A DNAzyme which binds to T-bet mRNA and functionally inactivates it, which comprises:
   (i) a catalytic domain with the nucleotide sequence GGCTAGCTACAACGA SEQ ID NO: 154 or a modified sequence with comparable biological effect, which cleaves the T-bet mRNA at every purine-pyrimidine binding site to which it is bound; and either
   (ii) a right substrate binding domain adjoining the 3'-end of the catalytic domain having polynucleotide sequence TGGGTTTCT; and
   (iii) a left substrate binding domain adjoining the 5'-end of the catalytic domain having polynucleotide sequence GGCAATGAA, both substrate binding domains being respectively complementary to two regions of the T-bet mRNA so that they hybridize with the mRNA, or;
   (iv) a right substrate binding domain adjoining the 3'-end of the catalytic domain having polynucleotide sequence GAACTGGGT; and
   (v) a left substrate binding domain adjoining the 5'-end of the catalytic domain having polynucleotide sequence TCACGGCAA, both substrate binding domains being respectively complementary to two regions of the T-bet mRNA so that they hybridize with the mRNA, and which is active in vivo.

2. A DNAzyme according to claim 1, which comprises the sequences td69 GGCAATGAA GGCTAGCTACAACGA TGGGTTTCT SEQ ID NO: 139 or td70 TCACGGCAA GGCTAGCTACAACGA GAACTGGGT SEQ ID NO: 140.

3. A DNAzyme according to claim 1, which cleaves the catalytic domain of the T-bet mRNA at every purine-uracil binding site.

4. A DNAzyme according to claim 1, which is stabilized against decomposition within the organism by introduction of a 3'-3' inversion.

5. A DNAzyme according to claim 1, which is stabilized against decomposition within the organism by the introduction of modified nucleotides or nucleotide compounds.

6. A DNAzyme according to claim 1, which includes an inverse thymidine on the 3' end and/or a FAM label on the 5' end.

7. A medicament containing a DNAzyme according to claim 1 and a pharmaceutically acceptable carrier.

8. A DNAzyme according to claim 1, which comprises the sequences td69 GGCAATGAA GGCTAGCTACAACGA TGGGTTTCT SEQ ID NO: 139.

* * * * *